(12) United States Patent
Winterberg et al.

(10) Patent No.: US 7,919,662 B2
(45) Date of Patent: *Apr. 5, 2011

(54) PROCESS FOR THE DISSOCIATION OF MTBE

(75) Inventors: Markus Winterberg, Datteln (DE); Walter Luh, Marl (DE); Silvia Santiago Fernandez, Oviedo (ES); Franz Nierlich, Marl (DE); Stephan Houbrechts, Duffel (BE); Dietrich Maschmeyer, Recklinghausen (DE); Horst-Werner Zanthoff, Mülheim a.d. Ruhr (DE); Wilfried Büschken, Haltern am See (DE)

(73) Assignee: Evonik Oxeno GmbH, Marl (DE)

( * ) Notice: Subject to any disclaimer, the term of this patent is extended or adjusted under 35 U.S.C. 154(b) by 761 days.

This patent is subject to a terminal disclaimer.

(21) Appl. No.: 11/838,340

(22) Filed: Aug. 14, 2007

(65) Prior Publication Data

US 2008/0058575 A1 Mar. 6, 2008

(30) Foreign Application Priority Data

Aug. 29, 2006 (DE) .......................... 10 2006 040 431

(51) Int. Cl.
*C07C 1/20* (2006.01)
(52) U.S. Cl. ............ 585/703; 585/1; 585/312; 585/638; 585/639; 585/640; 585/809
(58) Field of Classification Search .............. 585/1, 312, 585/639, 640, 703, 809, 638
See application file for complete search history.

(56) References Cited

U.S. PATENT DOCUMENTS

| 4,447,668 A * | 5/1984 | Smith et al. ................... 585/639 |
| 4,570,026 A * | 2/1986 | Keyworth et al. ............ 585/312 |
| 7,439,413 B2 * | 10/2008 | Malzkorn et al. ............. 585/639 |

(Continued)

FOREIGN PATENT DOCUMENTS

DE 102 38 370 A1 3/2004

(Continued)

OTHER PUBLICATIONS

Roberto Trotta, et al. "Case history: synthesis and decomposition of MTBE" Catalysis Today 34, Charpter 14, Elsevier, XP-002465780, 1997, pp. 447-455.

(Continued)

*Primary Examiner* — Prem C Singh
(74) *Attorney, Agent, or Firm* — Oblon, Spivak, McClelland, Maier & Neustadt, L.L.P.

(57) ABSTRACT

Isobutene is prepared by dissociation of MTBE in the gas phase, by a) fractional distillation of an MTBE-containing stream comprising feed MTBE (I) and a recycle stream (VIII) to give an MTBE-containing overhead stream (II) and a bottom stream (III) having a boiling point higher than MTBE, b) catalytic dissociation of the overhead stream (II) obtained in step a) to give a dissociation product (IV), c) separation by distillation of the dissociation product (IV) obtained in step b) into an overhead stream (V) comprising more than 90% by mass of isobutene and a bottom stream (VI) comprising diisobutene, MTBE and more than 50% of the methanol present in the dissociation product (IV), d) fractional distillation of the bottom stream obtained in step c) under conditions under which the methanol is obtained as bottom product (VII) and more than 99% of the MTBE is obtained in the overhead product (VIII), and e) recirculation of the overhead product (VIII) to step a).

18 Claims, 1 Drawing Sheet

U.S. PATENT DOCUMENTS

2006/0135833 A1     6/2006    Malzkorn et al.
2006/0264681 A1    11/2006    Obenaus et al.

FOREIGN PATENT DOCUMENTS

| | | |
|---|---|---|
| GB | 2 096 604 A | 10/1982 |
| WO | WO 2004/007412 A1 | 1/2004 |
| WO | WO 2004/018393 * | 3/2004 |

OTHER PUBLICATIONS

U.S. Appl. No. 11/614,275, filed Dec. 21, 2006, Praefke, et al.
U.S. Appl. No. 11/839,604, filed Aug. 16, 2007, Winterberg, et al.
U.S. Appl. No. 11/758,285, filed Jun. 5, 2007, Winterberg, et al.
U.S. Appl. No. 11/836,905, filed Aug. 10, 2007, Zanthoff, et al.
U.S. Appl. No. 11/839,597, filed Aug. 16, 2007, Fernandez, et al.

* cited by examiner

PROCESS FOR THE DISSOCIATION OF MTBE

BACKGROUND OF THE INVENTION

1. Field of the Invention

The present invention relates to a process for preparing isobutene by dissociation of methyl tert-butyl ether (MTBE).

2. Description of the Related Art

Isobutene is a starting material for the production of many products, e.g. for the production of butyl rubber, polyisobutylene, isobutene oligomers, branched $C_5$-aldehydes, $C_5$-carboxylic acids, $C_5$-alcohols and $C_5$-olefins. It is also used as an alkylating agent, in particular for the synthesis of tert-butylaromatics, and as intermediate for the production of peroxides. In addition, isobutene can be used as precursor for the preparation of methacrylic acid and its esters.

In industrial streams, isobutene frequently occurs together with saturated and unsaturated $C_4$-hydrocarbons. Owing to the small boiling point difference or the very low separation factor between isobutene and 1-butene in a distillation, isobutene cannot be separated economically from these mixtures. Isobutene is therefore usually isolated from industrial hydrocarbon mixtures by converting isobutene into a derivative which can easily be separated off from the remaining hydrocarbon mixture and redissociating the isolated derivative to form isobutene and the derivatizing agent.

Isobutene is usually separated off from $C_4$ fractions, for example the $C_4$ fraction from a steamcracker, as follows. After removal of the major part of the multiply unsaturated hydrocarbons, mainly butadiene, by extraction/extractive distillation or selective hydrogenation to linear butenes, the remaining mixture (raffinate I or hydrogenated cracking $C_4$) is reacted with alcohol or water. The use of methanol results in formation of methyl tert-butyl ether (MTBE) from isobutene and the use of water results in tert-butanol (TBA). After they have been separated off, both products can be dissociated to form isobutene in a reversal of their formation.

MTBE is cheaper than TBA because the reaction of isobutene-containing hydrocarbons with methanol is easier than with water and MTBE is produced in large quantities as a component of 4-stroke fuels. The production of isobutene from MTBE is therefore potentially more economical than from TBA if a similarly good process were to be available for the dissociation of MTBE as for the dissociation of TBA.

The dissociation of MTBE can be carried out in the liquid phase, the gas/liquid phase or the gas phase in the presence of acid catalysts. Regardless of the phase in which the dissociation is carried out, by-products are formed, although to differing extents. For example, undesirable $C_8$ and $C_{12}$ components can be formed by acid-catalysed dimerization or oligomerization of the isobutene formed in the dissociation. The undesirable $C_8$ components are mainly 2,4,4-trimethyl-1-pentene and 2,4,4-trimethyl-2-pentene, which will hereinafter be referred to collectively as diisobutene (DIB). In addition, part of the methanol formed in the dissociation can be converted into dimethyl ether.

For economical reasons (low price; good availability), the preparation of isobutene by dissociation of MTBE is not carried out using high-purity MTBE, for example MTBE/S from Oxeno Olefinchemie GmbH, but is carried out using MTBE of standard industrial quality (fuel grade). Industrial MTBE usually contains $C_8$ olefins, for example those mentioned above, 2-methoxybutane formed from linear butenes and methanol in the synthesis of MTBE, TBA, methanol and possibly $C_4$- and $C_5$-hydrocarbons as secondary components.

The components introduced via the starting MTBE and the by-products formed in the dissociation have to be separated from the isobutene and/or from recycle streams, so that a large part of the process costs (capital investments; operating costs) are incurred by the work-up section.

Various processes for preparing isobutene by dissociation of MTBE are known.

In EP 0 302 336, isobutene is obtained by dissociation of MTBE in a column which is a combination of a stirred vessel, a distillation column and an extraction column. The acid catalyst is located in the bottoms circuit. MTBE is fed into the bottoms circuit. Part of the circulating bottoms is taken off. The crude isobutene is extracted with water in the column. The aqueous, methanol-containing extract is taken off above the bottom. The isobutene is obtained as overhead product. The bottoms taken off are recirculated after discharge of a proportion thereof.

EP 0 068 785 claims a process in which the dissociation of MTBE is carried out in a continuously operated stirred vessel. Here, the acid catalyst is suspended in the starting material. Isobutene is separated off from the reaction mixture which distils off by means of a column from which it is obtained as overhead product. Part of the bottom product is recirculated to the stirred vessel. The other part is separated in a two-column system into an MTBE-containing stream which is recirculated to the stirred vessel and methanol which is taken off as a side stream. The way in which secondary components in the MTBE used and by-products formed are separated off is not disclosed.

In DE 32 10 435, MTBE is dissociated in a reactive distillation column. An isobutene mixture containing small amounts of methanol and traces of diisobutene is obtained as overhead product. The bottom product from the reactive distillation column is separated in a distillation column into an MTBE-containing stream which is recirculated to the reactive distillation column and a bottom product comprising methanol. The way in which by-products are separated off is not indicated.

The documents EP 0 633 048, DE 100 20 943 and DE 101 11 549 claim the preparation of isobutene by dissociation of MTBE in a reactive distillation column. The separation of secondary components from the dissociation mixture is not disclosed.

DE 102 27 350 and DE 102 27 351 describe processes for preparing isobutene by dissociation of MTBE in the gas phase. In both processes, the dissociation product is condensed and extracted with water. A water/methanol mixture is obtained as extract and is separated into methanol and water by distillation. The raffinate comprises isobutene, unreacted MTBE and secondary components. This mixture is separated by distillation into an overhead product which contains isobutene together with small amounts of dimethyl ether and a bottom product comprising MTBE and secondary components. No information is given about the use or work-up of the MTBE mixture obtained.

U.S. Pat. No. 6,049,020 describes, inter alia, the preparation of isobutene by dissociation of MTBE. Methanol is removed from the reaction product by extraction with water. The remaining raffinate is separated by distillation into an overhead product containing isobutene and a bottom product comprising unreacted MTBE and secondary components. The work-up of the MTBE mixture is not described. In U.S. Pat. No. 6,072,095 and U.S. Pat. No. 6,143,936, the work-up of the dissociation product is carried out analogously. The MTBE mixture containing the secondary components which is obtained is not worked up; it can be fed to a plant for preparing MTBE.

In the known processes for preparing isobutene by dissociation of MTBE, separation of by-products from unreacted MTBE is dispensed with because of the high cost. The MTBE stream containing the by-products is, after discharge of a proportion, recirculated to the dissociation and/or fed to a preceding MTBE plant. In any case, the isobutene yield based on the amount of MTBE fed into the isobutene plant is reduced in the known processes.

SUMMARY OF THE INVENTION

It was therefore an object of the present invention to provide an alternative process for preparing isobutene from MTBE, in which, in particular, the work-up of the bottom products obtained in the fractional distillation of the dissociation product is improved or simplified.

This and other objects have been achieved by the present invention the first embodiment of which includes a process for preparing isobutene by dissociation of MTBE in the gas phase, comprising:
 a) fractional distillation of an MTBE-containing stream comprising feed MTBE (I) and a recycle stream (VIII) to give an MTBE-containing overhead stream (II) and a bottom stream (III) having a boiling point higher than MTBE,
 b) catalytic dissociation of the overhead stream (II) obtained in step a) to give a dissociation product (IV),
 c) separation by distillation of the dissociation product (IV) obtained in step b) into an overhead stream (V) comprising more than 90% by mass of isobutene and a bottom stream (VI) comprising diisobutene, MTBE and more than 50% of the methanol present in the dissociation product (IV),
 d) fractional distillation of the bottom stream obtained in step c) under conditions under which the methanol is obtained as bottom product (VII) and more than 99% of the MTBE is obtained in the overhead product (VIII), and
 e) recirculation of the overhead product (VIII) to step a).

DETAILED DESCRIPTION OF THE INVENTION

It has now surprisingly been found that the work-up of the bottom products obtained in the fractional distillation of the dissociation product can be carried out using a column for separating high boilers from the stream which is fed to the dissociation, which is usually already present, and that a stream obtained as overhead product in the fractionation in only one column of the bottom product obtained in the fractionation of the dissociation product can be fed to this column.

The present invention accordingly provides a process for preparing isobutene by dissociation of MTBE in the gas phase, which is characterized in that it comprises the steps
 a) fractional distillation of an MTBE-containing stream comprising feed MTBE (I) and a recycle stream (VIII) to give an MTBE-containing overhead stream (II) and a bottom stream (III) having a boiling point higher than MTBE,
 b) catalytic dissociation of the overhead stream (II) obtained in step a) to give a dissociation product (IV),
 c) separation by distillation of the dissociation product (IV) obtained in step b) into an overhead stream (V) comprising more than 90% by mass of isobutene and a bottom stream (VI) comprising diisobutene, MTBE and more than 50% of the methanol present in the dissociation product (IV),
 d) fractional distillation of the bottom stream obtained in step c) under conditions under which the methanol is obtained as bottom product (VII) and more than 99% of the MTBE is obtained in the overhead product (VIII) and
 e) recirculation of the overhead product (VIII) to step a).

The process of the invention has the following advantages: not only $C_8$-olefins but also 2-methoxybutane present in industrial MTBE are separated off by means of the distillation step (a). The distillate (II) therefore contains only a small amount of components which could reduce the activity and operating life of the dissociation catalyst. Due to the low concentration of 2-methoxybutane (MSBE), only small amounts, if any, of linear butenes can be formed in the dissociation. An isobutene having a very low proportion of linear butenes, in particular 1-butene, can be prepared in this way. In step (d), methanol is obtained in such a high purity that it can be used for conventional industrial syntheses, for example esterifications or etherifications. Furthermore, the diisobutene formed as by-product in the dissociation is distilled off overhead in step (d) and is recirculated to the distillation step (a). The diisobutene present in the feed MTBE and the diisobutene formed by reaction can thus be separated off in one distillation step. The main advantage is, apart from the low capital investment, the high yield of isobutene based on the amount of MTBE fed to the plant. This advantage is particularly great when the isobutene plant is not part of an integrated production complex, for example a $C_4$ work-up with MTBE synthesis, but is a plant which uses MTBE delivered from outside (stand-alone plant).

The invention is described by way of example below without the invention, whose range of protection is defined by the claims and the description, being restricted thereto. The claims themselves are also part of the disclosure content of the present invention. If ranges, general formulae or classes of compounds are mentioned below, the disclosure encompasses not only the corresponding ranges or groups of compounds which are explicitly mentioned but also all subranges and subsets of compounds which can be obtained by leaving out individual values (ranges) or compounds, without these having been explicitly mentioned for reasons of clarity.

The process of the invention for preparing isobutene by dissociation of MTBE in the gas phase comprises the process steps
 a) fractional distillation of an MTBE-containing stream comprising feed MTBE (I) and a recycle stream (VIII) to give an MTBE-containing overhead stream (II) and a bottom stream (III) having a boiling point higher than MTBE,
 b) catalytic dissociation of the overhead stream (II) obtained in step a) to give a dissociation product (IV),
 c) separation by distillation of the dissociation product (IV) obtained in step b) into an overhead stream (V) comprising more than 90% by mass of isobutene and a bottom stream (VI) comprising diisobutene, MTBE and more than 50% of the methanol present in the dissociation product (IV),
 d) fractional distillation of the bottom stream obtained in step c) under conditions under which the methanol is obtained as bottom product (VII) and more than 99% of the MTBE is obtained in the overhead product (VIII) and
 e) recirculation of the overhead product (VIII) to step a).

Process Step a)

In process step a), a mixture of feed MTBE (I) from which, if desired, $C_4$- and $C_5$-hydrocarbons have been separated off and overhead product from the column K4 (VIII) is fractionated. Process step a) serves, in particular, to remove high boilers, especially diisobutene, from the process. Removal at this point (upstream of the dissociation reactor in process step b)) has the advantage that no or only very little diisobutene goes to process step b). This protects the catalyst against coating with diisobutene, as a result of which the risk of a reduction in the activity and shortening of the operating life of the catalyst is reduced. A further task of this column can be the partial or complete removal of 2-methoxybutane (MSBE); since MSBE can be dissociated into linear butenes and methanol in the reactor (R); an excessively high concentration of linear butenes may endanger the isobutene specification.

The separation by distillation of the MTBE-containing stream into an MTBE-containing overhead stream (II) and a bottom stream (III) comprising compounds having boiling points higher than that of MTBE in process step a) is carried out in at least one column, preferably in precisely one distillation column.

In the column, the MTBE-containing stream is preferably fractionally distilled to separate off high boilers, in particular diisobutene and/or 2-methoxybutane, from the MTBE. When, in particular, only diisobutene (DIB) is to be separated off in the column, it can be advantageous for the column to have from 15 to 60 theoretical plates, preferably from 20 to 55 theoretical plates and more preferably from 30 to 45 theoretical plates. The reflux ratio, which for the purposes of the present invention is defined as the mass flow of runback divided by the mass flow of distillate, is, depending on the number of theoretical plates realized, the composition of the MTBE used and the required purity, preferably set to a value of from 0.5 to 7, more preferably from 1 to 4.

If DIB and also MSBE are to be separated off in the column in process step a), the distillation column used preferably has from 50 to 140 theoretical plates, preferably from 60 to 120 theoretical plates and very particularly preferably from 80 to 110 theoretical plates. The reflux ratio is, depending on the number of theoretical plates realized, the composition of the MTBE used and the required purity, preferably from 1 to 20, more preferably from 3 to 10.

To increase the flexibility in respect of the quality of the feed MTBE (I) and the required purity of the isobutene prepared, it can be particularly advantageous to provide a column by means of which both substances can be separated off, i.e. a column which preferably has from 50 to 140 theoretical plates. Even if the removal of MSBE is not considered to be necessary, the larger column does not have to be a disadvantage since part of the higher capital investment for the larger column can be compensated for by energy savings (reduction in the reflux ratio).

The operating pressure can, irrespective of whether only DIB or also MSBE is/are to be separated off, preferably be from 0.1 to 2.0 MPa$_{(abs)}$. The pressure includes all values and subvalues therebetween, especially including 0.2, 0.3, 0.4, 0.5, 0.6, 0.7, 0.8, 0.9, 1, 1.1, 1.2, 1.3, 1.4, 1.5, 1.6, 1.7, 1.8, and 1.9 MPa$_{(abs)}$.

If the dissociation of the overhead product (II) is carried out in the gas phase at superatmospheric pressure in the dissociation reactor, it can be advantageous to carry out the distillation at a higher pressure. In this case, the overhead condenser is preferably operated as a partial condenser and the overhead product (II) is taken off in vapour form. If the reaction pressure in the dissociation reactor is, for example, 0.7 MPa$_{(abs)}$, the distillation pressure should preferably be at least 0.75 MPa$_{(abs)}$. At operating pressures of greater than 1.3 MPa$_{(abs)}$, ND steam can be generated by means of the heat of condensation and can be used for heating other columns of the process. Steam or heat transfer fluid can be used for heating the column, depending on the operating pressure selected. The bottom product (III) can contain MTBE in addition to the high boilers such as 2-methoxybutane and diisobutene. This mixture can be utilized thermally, be employed as starting material for a synthesis gas plant or be used directly or after hydrogenation as fuel component.

The composition of the feed to the column, i.e. the mixture of the streams I and VIII, can vary depending on the feed MTBE (I) and the degree of conversion of the MTBE in the dissociation reactor (R) (single pass). When an MTBE which corresponds to the typical Oxeno quality is used and the MTBE conversion is in the range from 50 to 95%, the feed to the column (e.g. K1) comprises from 85 to 97% by mass of MTBE and the methanol content is in the range from 2 to 12% by mass. The diisobutene content is in the range from 1500 to 5000 ppm by mass and the 2-methoxybutane content is in the range from 3500 to 5000 ppm by mass. Further components present are, inter alia, tert-butanol, water and linear butenes.

The bottom product (III) of the column (e.g. K1) contains the high boilers diisobutene and 2-methoxybutane together with MTBE. If primarily diisobutene is to be separated off in the column, the MTBE content of the bottom product can be reduced to values below 25% by mass. If 2-methoxybutane is also to be separated off, a higher MTBE content in the bottom product of from 60 to 85% by mass will advantageously be permitted to reduce the outlay for the separation because of the small boiling point difference between 2-methoxybutane and MTBE.

The composition of the overhead product (II) from the column (e.g. K1), which is passed to process step b), can vary depending on the feed MTBE (I), the degree of conversion of the MTBE in the dissociation reactor (R) (single pass) and the separation task in process step a). When an MTBE corresponding to the typical Oxeno quality (see starting materials) is used and the MTBE conversion is in the range from 50 to 95%, the overhead product (II) preferably comprises from 85 to 98% by mass of MTBE and the methanol content is preferably in the range from 2 to 12% by mass. The overhead product is preferably virtually diisobutene-free. The content of 2-methoxybutane can be, depending on the mode of operation of the column, preferably set to from 1000 ppm by mass to 1.5% by mass. Further components which can be present in the overhead product (II) are, inter alia, tert-butanol, water and linear butenes.

If an isobutene having a prescribed concentration of linear butenes, e.g. a concentration of linear butenes of less than 1000 ppm by mass, is to be prepared by the process of the invention, it can be advantageous to set the content of 2-methoxybutane in the overhead stream (II) to different values by variation of the distillation conditions. Depending on the degree of dissociation of MTBE in the downstream reactor R, different 2-methoxybutane concentrations can be permissible in the overhead stream (II). If a very complete conversion of the MTBE present in the stream (II) is sought in the reactor R, the content of 2-methoxybutane in stream (II) should not exceed 1000 ppm by mass in order to adhere to the isobutene specification of less than 1000 ppm by mass of linear butenes, since at a quantitative MTBE conversion the ratio of 2-methoxybutane to MTBE corresponds approximately to the ratio of linear butenes to isobutene in the dissociation product. On the other hand, if a lower MTBE conversion is set in the reactor R, the 2-methoxybutane concentration in the stream (II) can be more than 1000 ppm by mass, since MTBE is dissociated more quickly than 2-methoxybutane. However, the fractional distillation in step a) is preferably carried out so that the stream (II) obtained has a concentration of 2-methoxybutane based on MTBE of less than 2500 ppm by mass.

The ratio of the dissociation rate of MTBE to that of 2-methoxybutane can be dependent not only on the dissociation conditions but also on the catalyst used. The 2-methoxybutane concentrations which are permissible in the distillate (II) in order to achieve prescribed limit values for the concentration of 2-butenes in the isobutene can be determined for the given catalyst and conversion by means of simple preliminary tests. For example, when the catalysts described below, which formally comprise magnesium oxide, aluminium oxide and silicon oxide, are used, a 2-methoxybutane concentration of up to 2500 ppm by mass, in particular a concentration of 2000 ppm by mass (in each case based on MTBE), is permissible at MTBE conversions of from 85 to 95% without the isobutene specification being endangered.

In the present invention, "conversion" refers to how much of a reactant has reacted.

Process Step b)

The dissociation of the MTBE present in stream (II) into isobutene and methanol can be carried out in the liquid phase or gas/liquid mixed phase or in the gas phase in the presence of acid catalysts. In the process of the invention, the MTBE dissociation is preferably carried out in the gas phase. The MTBE dissociation is preferably carried out at a temperature in the range from 200 to 400° C., preferably from 230 to 350° C. The temperature includes all values and subvalues therebetween, especially including 220, 240, 250, 260, 280, 300, 320, 340, 350, 360, 380° C.

In the process of the invention, the dissociation of MTBE can be carried out using all known acid catalysts which are suitable for the dissociation of MTBE. Acid catalysts which can be used are, for example, metal oxides, mixed metal oxides, in particular ones which contain silicon oxide or aluminium oxide, acids on metal oxide supports or metal salts.

The dissociation in step b) is preferably carried out over a catalyst which has an activity in respect of the dissociation of MTBE which is at least 1%, preferably 5% and particularly preferably 10%, greater than the activity in respect of the dissociation of 2-methoxybutane. The activity of the catalyst can be determined in a simple manner by reacting a mixture of MSBE and MTBE under steady-state conditions over the selected catalyst and subsequently analysing the resulting reaction product for unreacted MTBE and MSBE.

In the process of the invention for the dissociation of MTBE, preferably for the dissociation of MTBE in the gas phase, preference is given to using catalysts which formally comprise magnesium oxide, aluminium oxide and silicon oxide. Such catalysts are described, for example, in U.S. Pat. No. 5,171,920 in Example 4 and in EP 0 589 557.

Particular preference is given to using catalysts which formally comprise magnesium oxide, aluminium oxide and silicon dioxide and have a proportion of magnesium oxide from 0.5 to 20% by mass, preferably from 5 to 15% by mass and particularly preferably from 10 to 15% by mass, a proportion of aluminium oxide of from 4 to 30% by mass, preferably from 10 to 20% by mass, and a proportion of silicon dioxide of from 60 to 95% by mass, preferably from 70 to 90% by mass. The amount of magnesium oxide includes all values and subvalues therebetween, especially including 1, 2, 4, 5, 6, 8, 10, 12, 14, 15, 16 and 18% by mass. The amount of aluminum oxide includes all values and subvalues therebetween, especially including 5, 6, 8, 10, 12, 14, 15, 16, 18, 20, 22, 24, 25, 26, and 28% by mass. The amount of silicon dioxide includes all values and subvalues therebetween, especially including 65, 70, 75, 80, 85, and 90% by mass.

It can be advantageous for the catalyst to contain an alkali metal oxide in addition to the magnesium oxide. This alkali metal oxide can, for example, be selected from among $Na_2O$ and $K_2O$. The catalyst preferably contains $Na_2O$ as alkali metal oxide. The preferred catalyst preferably has a BET surface area (determined volumetrically by means of nitrogen in accordance with DIN ISO 9277) of from 200 to 450 $m^2/g$, more preferably from 200 to 350 $m^2/g$. The BET includes all values and subvalues therebetween, especially including 220, 240, 250, 260, 280, 300, 320, 340, 350, 360, 380, 400, 420, 440 $m^2/g$. If the catalyst used according to the invention is applied as active composition to a support, only the active composition has a BET surface area in the range mentioned. On the other hand, the material composed of catalyst and support can, depending on the nature of the support, have a BET surface area which deviates significantly from these values, in particular a smaller BET surface area.

The pore volume of the catalyst is preferably from 0.5 to 1.3 ml/g, more preferably from 0.65 to 1.1 ml/g. The pore volume was preferably determined by the cyclohexane method. In this method, the sample to be tested is firstly dried to constant weight at 110° C. About 50 ml of the sample weighted to within 0.01 g are subsequently introduced into an impregnation tube which has been cleaned and dried to constant weight and has an outlet opening provided with a ground glass stopcock on the underside. The outlet opening is covered with a small polyethylene plate so as to prevent blockage of the outlet opening by the sample. After charging of the impregnation tube with the sample, the tube is carefully closed so as to be airtight. The impregnation tube is subsequently connected to a water pump, the ground glass stopcock is opened and a vacuum of 20 mbar is set in the impregnation tube by means of the water pump. The vacuum can be checked on a vacuum gauge connected in parallel. After 20 minutes, the ground glass stopcock is closed and the evacuated impregnation tube is subsequently connected to a cyclohexane reservoir which has been charged with a precisely measured volume of cyclohexane so that cyclohexane is sucked into the impregnation tube from the reservoir on opening the ground glass stopcock. The ground glass stopcock remains open until the entire sample is flooded with cyclohexane. The ground glass stopcock is subsequently closed again. After 15 minutes, air is carefully admitted into the impregnation tube and the cyclohexane which has not been absorbed is drained into the reservoir. Cyclohexane adhering to the inside of the impregnation tube or to the outlet opening or the connection with the cyclohexane reservoir can be conveyed into the reservoir by means of a single careful pressure pulse from a rubber bulb via the air admission line. The volume of the cyclohexane present in the reservoir is noted. The pore volume is given by the volume of cyclohexane absorbed, which is determined from the volume of cyclohexane in the reservoir before the measurement minus the volume of cyclohexane in the reservoir after the measurement, divided by the mass of the sample examined.

The mean pore diameter (preferably determined by a method based on DIN 66133) of the catalyst is preferably from 5 to 20 nm, more preferably from 8 to 15 nm. Particular preference is given to at least 50%, preferably more than 70%, of the total pore volume (sum of the pore volume of pores having a pore diameter of greater than or equal to 3.5 nm determined by mercury porosimetry in accordance with DIN 66133) of the catalyst being made up by pores having a diameter of from 3.5 to 50 nm (mesopores).

The process of the invention is preferably carried out using catalysts which have a mean particle size (determined by sieve analysis) of from 10 μm to 10 mm, preferably from 0.5 mm to 10 mm, particularly preferably a mean particle size of from 1 to 5 mm. Preference is given to using solid catalysts which have a mean particle size $d_{50}$ of from 2 to 4 mm, in particular from 3 to 4 mm.

The catalyst can be used as shaped bodies in the process of the invention. The shaped bodies can have any shape. The catalyst is preferably used as shaped bodies in the form of spheres, extrudates or pellets. The shaped bodies preferably have the abovementioned mean particle sizes.

The catalyst can also be applied to a support, e.g. a metal, plastic or ceramic support, preferably a support which is inert in respect of the reaction for which the catalyst is to be used. In particular, the catalyst used according to the invention can be applied to a metal support, e.g. a metal plate or a metal mesh. Such supports provided with the catalyst used according to the invention can, for example, be used as internals in reactors or reactive distillation columns. The supports can also be metal, glass or ceramic spheres or spheres of inorganic oxides. If the catalyst used according to the invention is applied to an inert support, the mass and composition of the inert support are not taken into account in determining the composition of the catalyst.

The particularly preferred catalysts which formally comprise magnesium oxide, aluminium oxide ($Al_2O_3$) and silicon dioxide can, for example, be produced by a process comprising the steps A1) treatment of an aluminosilicate with an acidic, aqueous magnesium salt solution and B1) calcination of the aluminosilicate treated with aqueous magnesium salt solution.

For the purposes of the present invention, aluminosilicates are compounds which are formally composed essentially of proportions of aluminium oxide ($Al_2O_3$) and silicon dioxide ($SiO_2$). However, the aluminosilicates can also contain small proportions of alkali metal oxides or alkaline earth metal oxides. Zeolites such as zeolites A, X, Y, USY or ZSM-5 or amorphous zeolites (for example MCM 41 from Mobil Oil) can also be used as aluminosilicates in the process. The aluminosilicates used in the process can be amorphous or crystalline. Suitable commercial aluminosilicates which can be used as starting materials in the process of the invention are, for example, aluminosilicates which have been prepared by precipitation, gelation or pyrolysis. The process is preferably carried out using aluminosilicates which comprise from 5 to 40% by mass, preferably from 10 to 35% by mass, of aluminium oxide and from 60 to 95% by mass, preferably from 65 to 90% by mass, of silicon dioxide (based on the dry mass; treatment: ignition at 850° C. for 1 hour). The amount of aluminum oxide includes all values and subvalues therebetween, especially including 5, 6, 8, 10, 12, 14, 15, 16, 18, 20, 22, 24, 25, 26, 28, 30, 32, 34, 35, 36, and 38% by mass. The amount of silicon dioxide includes all values and subvalues therebetween, especially including 65, 70, 75, 80, 85, and 90% by mass.

The composition of the aluminosilicates used or the catalysts obtained can, for example, be determined by classical analysis, fusion with Borax and XRF (X-ray fluorescence), energy-dispersive X-ray analysis, flame spectroscopy (Al and Mg, not Si), wet digestion and subsequent ICP-OES (Optical Emission Spectrometry with Inductively Coupled High-Frequency Plasma) or atomic absorption spectroscopy. A particularly preferred aluminosilicate which can be used in the process has a formal proportion of $Al_2O_3$ of 13% by mass and a proportion of silicon dioxide of 76% by mass. Such an aluminosilicate is marketed by Grace Davison under the trade name Davicat O 701.

The aluminosilicate can be used in a variety of forms in the process. Thus, the aluminosilicate can be used in the form of shaped bodies such as tablets, pellets, granules, rods or extrudates. However, the aluminosilicate can also be used as aluminosilicate powder. As starting material, it is possible to use powders having various mean particle sizes and various particle size distributions. In the production of shaped bodies, preference is given to using an aluminosilicate powder in which 95% of the particles have a mean particle size of from 5 to 100 µm, preferably from 10 to 30 µm and particularly preferably from 20 to 30 µm. The particle size can be determined, for example, by laser light scattering using a particle analyser from Malvern, e.g. the Mastersizer 2000.

The aqueous magnesium salt solution is produced using magnesium compounds which are water-soluble or are converted into water-soluble compounds by addition of an acid. The nitrates are preferably used as salts. Preference is given to using magnesium salt solutions which contain the salts of strong mineral acids, for example magnesium nitrate hexahydrate or magnesium sulphate heptahydrate, as magnesium salts. The acidic aqueous alkali metal and/or alkaline earth metal salt solution used preferably has a pH of less than 6, more preferably from <6 to 3 and particularly preferably from 5.5 to 3.5. The pH can be determined, for example, by means of a glass electrode or indicator paper. If the salt solution has a pH which is greater than or equal to 6, the pH can be adjusted by addition of an acid, preferably the acid whose alkali metal and/or alkaline earth metal salt is present in the solution. When the alkali metal and/or alkaline earth metal salt solution contains the nitrates as salts, nitric acid is preferably used as acid. The magnesium content of the magnesium salt solution used is preferably from 0.1 to 3 mol/l, preferably from 0.5 to 2.5 mol/l.

The treatment in step A1) can be carried out in various ways which are suitable for bringing the aluminosilicate into contact with the magnesium salt solution. Possible treatment methods are, for example, impregnation, steeping, spraying or irrigation of the aluminosilicate with the magnesium salt solution. It can be advantageous for the treatment of the aluminosilicate to be carried out so that the magnesium salt solution can act on the aluminosilicate for at least from 0.1 to 5 hours, preferably from 0.5 to 2 hours. Such a contact time can be particularly advantageous when the treatment is carried out by simple steeping.

In a preferred embodiment of step A1) of the process, the treatment of aluminosilicate, in particular shaped aluminosilicate bodies, with the magnesium salt solution can be carried out, for example, by vacuum impregnation in a vacuum impregnation unit suitable for this purpose. In this type of treatment, the aluminosilicate is firstly evacuated in the vacuum impregnation unit. The magnesium salt solution is subsequently sucked in up to above the upper surface of the bed of the support, so that all the aluminosilicate is covered with the solution. After a contact time which is preferably from 0.1 to 10 hours, more preferably from 0.5 to 2 hours, the solution which has not been taken up by the support is drained.

In a further preferred embodiment of step A1) of the process, the treatment of aluminosilicate, in particular shaped aluminosilicate bodies, with the alkali metal and/or alkaline earth metal salt solution, can be carried out, for example, by spraying or irrigation of the aluminosilicate. The spraying or irrigation of the aluminosilicate with the magnesium salt solution is preferably carried out by spraying or pouring the solution onto the aluminosilicate rotating in a drum. The treatment can be carried out in one action, i.e. the total amount of magnesium salt solution is added to the aluminosilicate at the beginning in one step. However, the salt solution can also be introduced in small portions by spraying or irrigation, the time of addition preferably being from 0.1 to 10 hours and more preferably from 1 to 3 hours. The amount of salt solution is preferably measured so that all of the solution is taken up by the aluminosilicate. Steeping in particular but also spraying or irrigation can be carried out in conventional industrial apparatuses, for example cone mixers or high-intensity mixers as are, for example, marketed by Eirich.

The treatment of the aluminosilicate with the magnesium salt solution in step A1) can be carried out in one step or in a plurality of substeps. In particular, it is possible to carry out the treatment in two or more substeps. In each of the individual substeps, it is possible to use the same magnesium salt solution in each case or else to use a magnesium salt solution having a different concentration in each substep. For example, it is possible to initially add only part of the magnesium salt solution to the aluminosilicate and, if desired after intermediate drying, to add the remainder of the magnesium salt solution to be used at the same temperature or a different temperature. It is not only possible for step A1) to be carried out in two or more substeps. It is likewise possible for the process to have a plurality of steps A1). In this case too, magnesium salt solutions having the same concentration or different concentrations can be used in the various steps A1).

The treatment in step A1) is preferably carried out at a temperature of from 10 to 120° C., more preferably from 10 to 90° C., particularly preferably from 15 to 60° C. and very particularly preferably at a temperature of from 20 to 40° C.

It can be advantageous for one or more additives to be added to or mixed into the aluminosilicate or the magnesium salt solution in step A1). Such additives can be, for example, binders, lubricants or shaping aids. A suitable binder can be, for example, boehmite or pesudoboehmite, as is marketed, for example, under the trade name Disperal (a boehmite having a formal $Al_2O_3$ content of about 77% by mass) by Sasol Deutschland GmbH. If boehmite, in particular Disperal, is added as binder, it is preferably added as a gel which can be obtained by, for example, stirring 197 parts by mass of Disperal into 803 parts by mass of a 1.28% strength by mass aqueous nitric acid, stirring vigorously at 60° C. for 3 hours, cooling to room temperature and replacing any water which has evaporated. As shaping aids, it is possible to use, for example, silicas, in particular pyrogenic silicas as are marketed, for example, by Degussa AG under the trade name Aerosil, bentonites, clays, kaolin, kaolinite, ball clay and other materials with which those skilled in the art are familiar for this purpose. As lubricant, whose use can be advantageous for improved tableting, it is possible to add, for example, graphite.

The addition of one or more of the abovementioned additives in step A1) can be carried out in various ways. In particular, the addition can be carried out during the treatment of the aluminosilicate with the magnesium salt solution. For example, aluminosilicate, additive and magnesium salt solution can be introduced into an industrial apparatus and subsequently mixed intimately. Another possibility is firstly to mix the aluminosilicate with the additive and subsequently add the magnesium salt solution. In a further variant, additive and magnesium salt solution can be added simultaneously to the aluminosilicate. The addition can in each case be carried out in one addition action, in portions or by spraying. The addition time is preferably less than 5 hours, more preferably less than 3 hours. It can be advantageous to mix the mixture for a further 0.1-10 hours, preferably 0.5-3 hours.

The process for producing the catalyst which is preferably used has at least one process step B1) in which the aluminosilicate which has been treated with alkali metal and/or alkaline earth metal salt solution is calcined. The calcination is preferably carried out in a gas stream, for example a gas stream containing, for example, air, nitrogen, carbon dioxide and/or one or more noble gases or consists of one or more of these components. The calcination is preferably carried out using air as gas stream.

The calcination in process step B1) is preferably carried out at a temperature of from 200 to 1000° C., more preferably from 300 to 800° C. The calcination is preferably carried out for a time of from 0.1 to 10 hours, more preferably from 1 to 5 hours. The calcination is particularly preferably carried out at a temperature of from 200 to 1000° C., preferably from 300 to 800° C., for from 0.1 to 10 hours, preferably from 1 to 5 hours.

Industrial calcination can preferably be carried out in a shaft furnace. However, the calcination can also be carried out in other known industrial apparatuses, for example fluidized-bed calciners, rotary tube furnaces or tray furnaces.

It can be advantageous for a step C1) in which the aluminosilicate which has been treated with magnesium salt solution is dried to be carried out between steps A1) and B1). Drying in step C1) can be carried out at a temperature of from 100 to 140° C. Drying is preferably carried out in a gas stream. Drying can, for example, be carried out in a gas stream which contains, for example, air, nitrogen, carbon dioxide and/or one or more noble gases or consists of one or more of these components. The intermediate step of drying after treatment with alkali metal and/or alkaline earth metal salt solution and before calcination makes it possible to ensure that large amounts of water vapour are not liberated during calcination. In addition, drying can prevent water from evaporating spontaneously during calcination and destroying the shape of the catalyst.

Depending on the desired shape of the catalyst, it can be advantageous to appropriately adapt the production process by means of additional process steps. If, for example, a pulverulent catalyst is to be produced by the process, the aluminosilicate can be used in the form of aluminosilicate powder and, for example, be treated with the magnesium salt solution (e.g. by impregnation) in a cone mixer, optionally dried and subsequently calcined. However, a pulverulent catalyst can also be produced by processing a shaped catalyst body by milling and sieving to give a pulverulent catalyst.

The shaped catalyst bodies can, for example, be in the form of extrudates, spheres, pellets or tablets. To obtain the shaped catalyst (shaped catalyst body), further process steps such as shaping, milling or sieving can be carried out in addition to the process steps of treatment, drying and calcination, depending on the respective shaping variant. Shaping aids can be introduced into the process at various points. The shaped catalyst bodies can be produced in various ways:

In a first variant, shaped catalyst bodies, in particular shaped catalyst bodies to be used according to the invention, can be obtained by treating shaped aluminosilicate bodies with an acidic aqueous magnesium salt solution, optionally drying them and subsequently calcining them.

In a second embodiment, a shaped catalyst body can be obtained by firstly treating an aluminosilicate powder with an acidic aqueous magnesium salt solution, then drying it if desired and subsequently calcining it and then processing the resulting catalyst powder by industrially customary methods such as compacting, extrusion, pelletization, tableting, granulation or coating to produce shaped catalyst bodies. Additives required for shaping, e.g. binders or further auxiliaries, can be added at various points in the production process, e.g. in process step A1). In the production of a shaped body from an aluminosilicate powder as starting material, it is possible to start out from powders having various mean particle sizes and various particle size distributions. In the production of shaped bodies, preference is given to using an aluminosilicate powder in which 95% of the particles have a particle size of from 5 to 100 µm, preferably from 10 to 30 µm and particularly preferably from 20 to 30 µm (determined by laser light scattering, see above).

In a third embodiment of the process, pellets of the catalyst can be obtained by treating an aluminosilicate powder with an acidic aqueous magnesium salt solution in process step A1), optionally drying it (process step C1)) and subsequently calcining it in process step B1) and then pelletizing the resulting catalyst powder, e.g. in an Eirich mixer, with addition of binders and drying the resulting pellets in a further process step C1) and subsequently calcining them in a further process step B1).

In a fourth embodiment of the production process, pellets of the catalyst can be obtained by mixing an aluminosilicate powder, binder and acidic aqueous magnesium salt solution in process step A1) and pelletizing the treated aluminosilicate powder, e.g. in an Eirich mixer, and drying the resulting moist pellets in process step C1) and subsequently calcining them in a gas stream in process step B1).

In a fifth embodiment of the production process, tablets of the catalyst can be obtained by mixing an aluminosilicate powder, binder, optionally lubricant and acidic aqueous magnesium salt solution in process step A1) and pelletizing the treated aluminosilicate powder, e.g. in an Eirich mixer, to form micropellets having a mean diameter of preferably from 0.5 to 10 mm, more preferably from 1 to 5 mm and particularly preferably from 1 to 3 mm (determination of the particle size can, for example, be carried out by sieve analysis) and drying the resulting moist pellets in process step C1) and subsequently, if desired, calcining them in a gas stream in process step B1). The pellets obtained can then, if this has not yet occurred in process step A1), be mixed with a lubricant such as graphite and subsequently be tableted on a commercial tableting press, e.g. a rotary press. The tablets can then, if a process step B1) has not yet been carried out, be calcined in process step B1) or optionally be after-calcined.

In a sixth embodiment of the production process, tablets of the catalyst can be obtained by milling preshaped shaped catalyst bodies, as can be obtained, for example, as pellets in embodiment three and four, and sieving the granules/powder obtained so as to give a tabletable granular catalyst material and mixing lubricant into this granular material. The granular material which has been prepared in this way can subsequently be tableted. The tablets can then, if a process step B1) has not yet been carried out, be calcined in process step B1). The addition of a lubricant can be omitted if a lubricant has already been added in the production of the pellets, e.g. in process step A1).

In a seventh embodiment of the process of the invention, materials/supports coated with the catalyst can be produced. In this embodiment, a catalyst powder will firstly be produced by treating an aluminosilicate powder with an acidic aqueous magnesium salt solution in process step A1), optionally drying it (process step C1)) and optionally calcining it (process step B1)). The catalyst powder obtained in this way is subsequently suspended in a suspension medium such as water or alcohol, if desired with addition of a binder to the suspension. The suspension produced in this way can then be applied to any desired material. After application of the catalyst suspension, the material is optionally dried (process step C1)) and subsequently calcined (process step B1)). Materials/supports coated with the preferred catalyst can be provided in this way. Such materials/supports can be, for example, metal plates or meshes as can be used as internals in reactors or columns, in particular reactive distillation columns, or else metal, glass or ceramic spheres or spheres composed of inorganic oxides.

In an eighth embodiment of the production process, extrudates of the catalyst, in particular the catalyst to be used according to the invention, can be obtained by mixing an aluminosilicate powder, acidic aqueous alkali metal and/or alkaline earth metal salt solution, binder such as Disperal and further shaping aids customary for extrusion, for example clays such as bentonite or attapulgite, in process step A1) in a kneader or Eirich mixer and extruding the mixture in an extruder to give extrudates having a mean diameter of preferably from 0.5 to 10 mm, more preferably from 1 to 5 mm and particularly preferably from 1 to 3 mm, and optionally drying the resulting moist extrudates in process step C1) and subsequently calcining them in a gas stream in process step B1).

The dissociation of MTBE is particularly preferably carried out using these preferred catalysts (Mg/Al/Si mixed oxide) in the temperature range from 200 to 400° C., preferably in the temperature range from 230 to 350° C.

The reaction pressure in step b) is preferably from 0.1 to 10 $MPa_{(abs)}$, preferably from 0.5 to 0.8 $MPa_{(abs)}$. The dissociation is preferably carried out at a WHSV (weight hourly space velocity) of from 0.1 to 5 $h^{-1}$, preferably from 1 to 3 $h^{-1}$ (kg of MTBE per kg of catalyst per hour). The MTBE conversion in a single pass is preferably from 50 to 98%, more preferably from 80 to 95%. The dissociation can be carried out in customary reactors, e.g. in a tube reactor, shell-and-tube reactor, shaft furnace or fluidized-bed reactor or a combination thereof.

The dissociation in the gas phase is preferably carried out in a reactor which is provided with a heating jacket and is heated by means of a liquid heat transfer medium, the dissociation being carried out so that the temperature drop in the catalyst zone/reaction zone at any desired point relative to the inlet temperature is less than 50° C., preferably less than 40° C. and particularly preferably from 1 to 30° C., so that the reaction mixture in the reactor and the heat transfer medium in the jacket flow in cocurrent through the reactor and so that the difference in temperature of the heat transfer medium between inflow point to the reactor and exit from the reactor is less than 40° C. The maximum temperature drop can be set by means of numerous parameters, e.g. by means of the temperature of the heat transfer medium used for heating and via the rate at which the heat transfer medium flows through the jacket.

The inlet temperature of the gaseous starting material, in particular in this preferred embodiment of process step b) according to the invention, is preferably above 200° C., more preferably above 230° C. and particularly preferably above 250° C. The inlet temperature of the starting material can be set in a heater located upstream of the reactor. When fresh catalyst is used in the MTBE dissociation, in particular when fresh magnesium oxide/aluminium oxide/silicon oxide catalyst is used, the inlet temperature is preferably in the range from 250 to 270° C. It can be advantageous to increase the inlet temperature up to 400° C. during operation as the catalyst becomes increasingly deactivated in order to keep the conversion constant. When the conversion can no longer be kept constant after reaching 400° C., it can be advantageous to replace all or part of the catalyst.

The reactor is, especially in the case of this preferred embodiment of process step b) according to the invention, preferably operated at a space velocity (weight hourly space velocity (WHSV) in kilogram of starting material per kilogram of catalyst per hour) of from 0.1 to 5 $h^{-1}$, in particular from 1 to 3 $h^{-1}$, in a single pass.

The reactor can, especially in this preferred embodiment of process step b) according to the invention, be arranged in any direction in space. If the reactor has reaction tubes, these can likewise point in any direction in space. However, the reactor is preferably erected so that the reactor or the reaction tubes are vertical. In the case of a vertical reactor, the heat transfer medium is preferably fed in at the highest point or in the vicinity of the highest point of the jacket and taken off at the lowest point or in the vicinity of the lowest point of the reactor, or vice versa. The reaction mixture in the reaction zone and the heat transfer medium in the jacket preferably flow through the reactor in the same direction. The heat transfer medium and the reaction mixture particularly preferably flow through the jacket of the reactor and the reaction zone of the reactor, respectively, from the top downwards.

To achieve more uniform heating of the reaction zone, it can be advantageous to feed the heat transfer medium into the reactor not only at one point but at a plurality of points at about the same height. To avoid a relatively large temperature drop in the middle tubes compared to tubes around the outside when a shell-and-tube reactor is used, it can be advantageous to provide nozzles which favour transport of the heat transfer medium to the middle tubes in the inlet or inlets for the heat transfer medium. In this way, temperature fluctuations over the cross section of the bundle of tubes can be avoided.

The heat transfer medium can leave the reactor at one or more point(s). If the heat transfer medium flows through the reactor from the top downwards, it should be ensured by constructional measures that the reaction zones, e.g. the reaction tubes, are completely surrounded by flowing heat transfer medium.

The heat transfer medium can be brought to the desired temperature outside the reactor by means of direct or indirect heating and pumped through the reactor.

As heat transfer medium, it is possible to use salt melts, water or heat transfer fluids. Use of heat transfer fluids is advantageous for the temperature range from 200 to 400° C., since heating circuits using them require a lower capital investment compared to other engineering solutions. Heat transfer fluids which can be used are, for example, those which are marketed under the trade names Marlotherm (e.g. Marlotherm SH from Sasol Olefins & Surfactants GmbH), Diphyl (from Bayer), Dowtherm (from Dow) or Therminol (from Therminol). These synthetic heat transfer fluids are based essentially on thermally stable cyclic hydrocarbons.

The heat transfer medium is preferably fed into the heating jacket of the reactor at a temperature which is from 10 to 40° C., preferably from 10 to 30° C., higher than the temperature of the starting material flowing into the reactor. The difference in temperature of the liquid heat transfer medium over the reactor, i.e. between the inlet temperature of the heat transfer medium on entering the heating jacket and the outlet temperature of the heat transfer medium on leaving the heating jacket, is preferably less than 40° C., more preferably less than 30° C. and particularly preferably from 10 to 25° C. The temperature difference can be set via the mass flow of heat transfer medium per unit time (kilogram per hour) through the heating jacket.

The preferred embodiment of process step b) according to the invention can be carried out in all suitable reactors which are provided with a heating jacket and can be heated by means of a liquid heat transfer medium. Such reactors have a reaction zone in which the catalyst is present (catalyst zone) which is separated physically from a heating jacket through which the heat transfer medium flows. The process of the invention is preferably carried out in a plate reactor, in a tube reactor, in a plurality of tube reactors or plate reactors connected in parallel or in a shell-and-tube reactor. The process of the invention is preferably carried out in a shell-and-tube reactor.

It may be pointed out that the hollow bodies in which the catalyst is present do not have to be tubes in the normal sense of the word. The hollow bodies can also have noncircular cross sections. They can, for example, be elliptical or triangular.

The materials for construction of the reactor, in particular the material which separates the reaction zone from the heating jacket, preferably have a high thermal conductivity coefficient (greater than 40 W/(m·K)). Preference is given to using iron or an iron alloy, e.g. steel, as material having a high thermal conductivity coefficient.

If the process of the invention is carried out in a shell-and-tube reactor, the individual tubes preferably have a length of from 1 to 15 m, more preferably from 3 to 9 m and particularly preferably from 5 to 9 m. The individual tubes in a shell-and-tube reactor used in the process of the invention preferably have an internal diameter of from 10 to 60 mm, more preferably from 20 to 40 mm and particularly preferably from 24 to 35 mm. It can be advantageous for the individual tubes of the shell-and-tube reactor used in the process of the invention to have a thickness of the tube wall of from 1 to 4 mm, preferably from 1.5 to 3 mm.

In a shell-and-tube reactor used in the preferred embodiment of process step b) according to the invention, the tubes are preferably arranged in parallel. The tubes are preferably arranged uniformly. The arrangement of the tubes can be, for example, square, triangular or diamond-shaped. Particular preference is given to an arrangement in which the virtually connected middle points of three mutually adjacent tubes form an equilateral triangle, i.e. the tubes have the same spacing. The process of the invention is preferably carried out in a shell-and-tube reactor in which the tubes have a spacing of from 3 to 15 mm, particularly preferably from 4 to 7 mm.

The dissociation in step b) is preferably carried out under conditions under which the conversion of MTBE is greater than the conversion of 2-methoxybutane. In this simple fashion, it can be ensured that the dissociation product has a concentration of less than 1000 ppm by mass of linear butenes based on the $C_4$-olefin fraction, even when the overhead stream (II) has a proportion of 2-methoxybutane (MSBE) of greater than 1000 ppm by mass based on MTBE. Depending on the proportion of MSBE present in the overhead stream (II), it may be necessary to set conditions under which the conversion of MSBE is significantly, i.e., for example, at least 50%, lower than the conversion of MTBE. These conditions can be determined by means of simple preliminary tests.

The main reaction in process step b) of the process of the invention is the dissociation of MTBE into isobutene and methanol. Depending on the MTBE conversion set, the dissociation product preferably has a residual MTBE content of from 2 to 43% by mass, more preferably from 3 to 25% by mass and particularly preferably from 5 to 15% by mass. The methanol content of the dissociation product (IV) is preferably from 25 to 37% by mass, more preferably from 30 to 37% by mass. The isobutene content of the dissociation product is preferably from 28 to 61% by mass, more preferably from 50 to 60% by mass. The formation of diisobutene from isobutene and the reaction of methanol to form dimethyl ether can occur as secondary reactions. Any 2-methoxybutane present in the starting material (II) fed to process step b) can be partly dissociated to form linear butenes and tert-butanol (TBA) present can be dissociated into isobutene and water. Diisobutene, dimethyl ether, linear butenes and water, inter alia, can therefore be present in the dissociation product (IV) as further components formed by reaction.

Process Step c)

To work up the dissociation product mixture further, the dissociation product (IV) is fractionated in a further distillation step c) to give an isobutene-containing overhead stream (V) and a bottom stream (VI) comprising unreacted MTBE. The separation of the dissociation product (IV) into an isobutene-containing overhead stream (V) and a bottom stream (VI) comprising unreacted MTBE by distillation in process step c) is carried out in at least one column, preferably precisely one distillation column.

A distillation column which is preferably used in process step c) preferably has from 20 to 55 theoretical plates, more preferably from 25 to 45 theoretical plates and particularly preferably from 30 to 40 theoretical plates. The reflux ratio is, depending on the number of theoretical plates realized, the composition of the output from the reactor and the required purities of distillate and bottom product, preferably less than 5, more preferably less than 1. The operating pressure of the column K2 can preferably be set to from 0.1 to 2.0 $MPa_{(abs)}$. The pressure includes all values and subvalues therebetween, especially including 0.2, 0.3, 0.4, 0.5, 0.6, 0.7, 0.8, 0.9, 1, 1.1, 1.2, 1.3, 1.4, 1.5, 1.6, 1.7, 1.8, and 1.9 $MPa_{(abs)}$.

To save a compressor, it can be advantageous to operate the column at a pressure which is lower than the pressure at which the dissociation reactor R in process step b) is operated. To be able to condense isobutene by means of cooling water, a pressure of about 0.5 $MPa_{(abs)}$ is necessary. If the dissociation in process step b) is carried out at, for example, a pressure of 0.65 $MPa_{(abs)}$, it can be advantageous for the distillation column of process step c) to be operated at a pressure of from 0.55 to 0.6 $MPa_{(abs)}$. Heating of the vaporizer can be effected using, for example, 0.4 MPa steam. The bottom product (VI) preferably contains unreacted MTBE, methanol and possibly by-products such as diisobutene and 2-methoxybutane. The overhead product is preferably isobutene having a purity of greater than 95% by mass, based on the total overhead product.

Process step c) can optionally be carried out in at least one column configured as a reactive distillation column. This embodiment of the process of the invention has the advantage that the MTBE conversion in the overall process can be increased by part of the MTBE which has not been reacted in process step b) being dissociated into isobutene and methanol in the reaction part of the reactive distillation column of process step c).

As catalysts in the reaction part of the reactive distillation column, it is possible to use all catalysts which are suitable for the dissociation of MTBE. Preference is given to using acid catalysts as catalysts. A particularly preferred group of acid catalysts for use in the reaction part of the reactive distillation column are solid, acidic ion-exchange resins, in particular ones having sulphonic acid groups. Suitable acidic ion-exchange resins are, for example, those which are prepared by sulphonation of phenol/aldehyde condensates or of cooligomers of aromatic vinyl compounds. Examples of aromatic vinyl compounds for preparing the cooligomers are: styrene, vinyltoluene, vinylnaphthalene, vinylethylbenzene, methylstyrene, vinylchlorobenzene, vinylxylene and divinylbenzene. In particular, the cooligomers formed by reaction of styrene with divinylbenzene are used as precursor for preparing ion-exchange resins having sulphonic acid groups. The resins can be produced in gel, macroporous or sponge form. The properties of these resins, in particular the specific surface area, porosity, stability, swelling or shrinkage and exchange capacity, can be varied by means of the production process.

The ion-exchange resins can be used in their H form in the reaction section of the reactive distillation column. Strong acid resins of the styrene-divinylbenzene type are, inter alia, sold under the following trade names: Duolite C20, Duolite C26, Amberlyst 15, Amberlyst 35, Amberlyst 46, Amberlite IR-120, Amberlite 200, Dowex 50, Lewatit SPC 118, Lewatit SPC 108, K2611, K2621, OC 1501.

The pore volume of the ion-exchange resins used is preferably from 0.3 to 0.9 ml/g, in particular from 0.5 to 0.9 ml/g. The particle size of the resin is preferably from 0.3 mm to 1.5 mm, more preferably from 0.5 mm to 1.0 mm. The particle size distribution can be selected so as to be relatively narrow or relatively broad. Thus, for example, it is possible to use ion-exchange resins having a very uniform particle size (monodisperse resins). The capacity of the ion exchanger, based on the form as supplied, is preferably from 0.7 to 2.0 eq/l, in particular from 1.1 to 2.0 eq/l.

In the reaction part of a column which has optionally been configured as a reactive distillation column in process step c), the catalyst can either be integrated into the packing, for example into KataMax® (as described in EP 0 428 265) or KataPak® (as described in EP 0 396 650 or DE 298 07 007.3 U1) packings, or be polymerized onto shaped bodies (as described in U.S. Pat. No. 5,244,929).

The reactive distillation column preferably has a region of purely distillative separation above the catalyst packing. The zone above the catalyst packing preferably has from 5 to 25, in particular from 5 to 15, theoretical plates. The separation zone below the catalyst preferably encompasses from 5 to 35, more preferably from 5 to 25, theoretical plates. The feed to the reactive distillation column can be introduced above or below, preferably above, the catalyst zone.

The conversion of the MTBE into isobutene and methanol in the reactive distillation is preferably carried out in a temperature range from 60 to 140° C., more preferably from 80 to 130° C., particularly preferably from 90 to 110° C. (temperature in the region of the column in which the catalyst is present; the temperature at the bottom can be significantly higher).

As regards the operating pressure of the reactive distillation column, it is in principle possible to choose operating conditions similar to those for the above-described embodiment as pure distillation column. Thus, preference is given to setting an operating pressure in the reactive distillation column of from 0.1 to 1.2 $MPa_{(abs)}$. To save a compressor, it can be advantageous to operate the column at a pressure lower than the pressure at which the dissociation reactor R in process step b) is operated. To be able to condense isobutene by means of cooling water, a pressure of about 0.5 $MPa_{(abs)}$ is necessary. If the dissociation in process step b) is, for example, carried out at a pressure of 0.65 $MPa_{(abs)}$, it can be advantageous for the distillation column of process step c) to be operated at a pressure of from 0.55 to 0.6 $MPa_{(abs)}$. The vaporizer can be heated using, for example, steam.

The hydraulic loading in the catalytic packing of the column is preferably from 10% to 110%, more preferably from 20% to 70%, of its flooding point loading. For the purposes of the present invention, the hydraulic loading of a distillation column is the uniform hydrodynamic loading of the column cross section by the ascending vapour stream and the descending liquid stream. The upper loading limit is the maximum loading by vapour and liquid runback above which the separating action decreases as a result of entrainment or backing-up of the liquid runback by the ascending vapour stream. The lower loading limit is the minimum loading below which the separating action decreases or breaks down as a result of irregular flow or empty running of the column, e.g. the trays. (Vauck/Müller, "Grundoperationen chemischer Verfahrenstechnik", p. 626, VEB Deutscher Verlag für Grundstoffindustrie.)

When the column in process step c) is configured as a reactive distillation column, the bottom product (VI) obtained preferably likewise contains unreacted MTBE and methanol and possibly by-products such as diisobutene and 2-methoxybutane. The overhead product preferably comprises isobutene having a purity of greater than 95% by mass.

The overhead product (V) which is obtained in process step c) and preferably comprises more than 95% by mass of isobutene can be used directly as commercial product or be purified further.

Since isobutene forms a minimum boiling point azeotrope with methanol, the overhead product (V) obtained in process step c) contains not only the main product isobutene but also, in particular, methanol. Further components which can be present in the overhead product (V) are, for example, dimethyl ether, which can be formed, for example, by condensation of methanol, and linear butenes (1-butene, cis-2-butene, trans-2-butene), which can be formed, for example, by decomposition of 2-methoxybutane, and water.

Part of the dimethyl ether can optionally be separated off from the overhead product (V) in process step c) by operating the condenser on the distillation column or reactive distillation column as a partial condenser. The $C_4$ fraction present in the overhead product can be condensed in this and part of the dimethyl ether present in the overhead product (V) can be taken off in gaseous form.

The formation of linear butenes can be avoided by complete removal of 2-methoxybutane in process step a). However, in order to limit the distillation costs in process step a), it can be advantageous to permit a low concentration of 2-methoxybutane in stream (II). This is possible, in particular, when a catalyst which decomposes MTBE more quickly than 2-methoxybutane is used in process step b), so that the ratio of linear butenes to isobutene in stream (V) is smaller than the ratio of 2-methoxybutane to MTBE in stream (II). The required isobutene quality in respect of linear butenes can thus be set by control of the distillation in the column of process step a) and by means of the degree of conversion of MTBE (in a single pass).

The content of linear butenes in the overhead product (V) obtained in process step c) is, based on the $C_4$-olefin fraction, preferably less than 10 000 ppm by mass, more preferably less than 5000 ppm by mass and particularly preferably less than 1000 ppm by mass. The content of 1-butene in the overhead fraction (V) based on the $C_4$-olefin fraction is preferably less than 5000 ppm by mass, more preferably less than 1000 ppm by mass and particularly preferably less than 500 ppm by mass. The content of 2-butenes (sum of the two 2-butenes) is, based on the $C_4$-olefin fraction, preferably likewise less than 5000 ppm by mass, more preferably less than 2000 ppm by mass and particularly preferably less than 500 ppm by mass.

Process Steps d) and e)

The bottom product (VI) obtained in process step c) contains the MTBE which has not been reacted in process step b) and the major part of the methanol formed in the dissociation of the MTBE. By-products, for example diisobutene, and/or 2-methoxybutane may also be present in the bottom product.

The bottom stream (VI) obtained in process step c) is separated by distillation into a methanol-containing bottom stream (VII) and an MTBE-containing overhead stream (VIII) in process step d). The separation by distillation is preferably carried out under such conditions that very pure methanol is obtained as bottom product (VII) and MTBE makes up more than 99% of the overhead product (VIII). The overhead product VIII is recirculated to process step a) (see FIG. 1 or 2).

Table 1 below shows the boiling points of the pure substances MTBE, 2-methoxybutane, methanol, tert-butanol and diisobutene at 0.1 $MPa_{(abs)}$. In the case of diisobutene which occurs as two isomers, the boiling point of 2,4,4-trimethylpent-1-ene has been given by way of example. It can be seen that the boiling point rises in the order MTBE, 2-methoxybutane, methanol, tert-butanol and diisobutene. However, the components MTBE, 2-methoxybutane and diisobutene at the same time form a minimum boiling point azeotrope with methanol. The boiling points of these azeotropes and the compositions are likewise shown in Table 1, the azeotropes having been calculated by the Property Method "UNIFAC-DMD" (see J. Gmehling, J. Li, and M. Schiller, Ind. Eng. Chem. Res. 32, (1993), pp. 178-193) using the steady-state simulation program ASPEN Plus (Version 12.1 from AspenTech). Under these boundary conditions, the MTBE-methanol azeotrope is the lowest boiler in the system and can be obtained as overhead product in a column used in process step d). However, if virtually pure methanol is to be generated as bottom product, the 2-methoxybutane-methanol and diisobutene-methanol azeotropes additionally have to be distilled off overhead. The only secondary component remaining in the bottom product is, apart from the water which is not shown in Table 1 and the product of value methanol, tert-butanol.

TABLE 1

Boiling points of the pure substances and the azeotropes with methanol at 0.1 $MPa_{(abs)}$; the azeotropes were calculated by the Property Method "UNIFAC-DMD"

| | Boiling point [° C.] | Composition [% by mass] |
|---|---|---|
| MTBE + methanol azeotrope | 50.50 | MTBE/methanol: 86.22/13.78 |
| 2-Methoxybutane + methanol azeotrope | 54.06 | 2-Methoxybutane/methanol: 80.40/19.60 |
| Pure MTBE | 54.64 | — |
| Methanol + diisobutene azeotrope | 59.22 | Methanol/diisobutene 47.84/52.16 |
| Pure 2-methoxybutane | 60.77 | — |
| Pure methanol | 64.19 | — |
| Pure tert-butanol | 82.14 | — |
| Pure diisobutene | 101.06 | — |

The fractional distillation of the bottom stream (VI) in process step d) is preferably carried out in a column, preferably in precisely one distillation column. A distillation column which is preferably used in process step c) preferably has from 20 to 75 theoretical plates, more preferably from 30 to 65 theoretical plates and particularly preferably from 35 to 50 theoretical plates. It can be advantageous for the column in process step d) to be operated, depending on the number of theoretical plates realized and the MTBE conversion achieved in process step b), at a reflux ratio of less than 10, preferably from 0.5 to 5. The operating pressure of the column in process step d) according to the invention is preferably set to a value in the range from 0.05 to 1 $MPa_{(abs)}$, more preferably from 0.1 to 0.3 $MPa_{(abs)}$. The pressure includes all values and subvalues therebetween, especially including 0.1, 0.2, 0.3, 0.4, 0.5, 0.6, 0.7, 0.8, 0.9 $MPa_{(abs)}$.

The column can be heated using, for example, 0.4 MPa steam. The condensation can, depending on the operating pressure selected, be effected by means of cooling brine, cooling water or air.

The bottom product produced in process step d) preferably contains more than 99% by mass of methanol. The TBA content of the bottom product is preferably from 500 to 2000 ppm by mass and the water content is preferably from 0.5 to 0.8% by mass. The methanol thus has a purity high enough for it to be suitable as commercial product and to be able to be used for customary industrial syntheses, for example esterifications or etherifications. If necessary, the methanol can, however, also be concentrated to still higher purities in a further distillation step.

The overhead product (VIII) obtained in the distillation in process step d) is, in process step e), recirculated to process step a). The overhead product is preferably mixed with the feed MTBE to form the MTBE stream (I) and this is used as starting stream in process step a). The overhead product (VIII) contains essentially the MTBE present in the feed stream (VI), the 2-methoxybutane and the diisobutene. The methanol content can vary in the range from 20 to 30% by mass. In process step a), diisobutene and possibly also 2-methoxybutane can, as described above, be separated off via the bottom product and be discharged from the process.

Process Step f) Isobutene Work-Up

Commercial isobutene grades are usually virtually free of methanol. The methanol can be separated off from the stream (V) obtained in process step c) by methods known per se, for example by extraction. The extraction of methanol from stream (V) can be carried out using, for example, water or an aqueous solution as extractant, e.g. in an extraction column. The extraction is preferably carried out using water or an aqueous solution in an extraction column which preferably has from 4 to 16 theoretical plates. The extractant preferably flows through the extraction column in countercurrent relative to the stream to be extracted. The extraction is preferably carried out at a temperature of from 15 to 50° C., more preferably from 25 to 40° C. For example, when an extraction column having more than 6 theoretical plates is used and is operated at a pressure of 0.9 MPa$_{(abs)}$ and a temperature of 40° C., a water-saturated isobutene having an isobutene content above 99% by mass can be obtained.

The methanol-containing water extract obtained in the extraction can be separated into water and methanol by distillation. The water can be recirculated as extractant to the extraction stage. The methanol can be utilized for customary industrial syntheses, for example esterifications or etherifications.

The moist isobutene stream from the extraction column can be worked up in a further distillation column by removal of water and optionally of dimethyl ether to give dry isobutene. The dry isobutene is obtained as bottom product here. In the condensation system at the top of the column, water can be taken off in liquid form and dimethyl ether can be taken off in gaseous form after a phase separation. A distillation column which is preferably used for drying preferably has from 30 to 80 theoretical plates, preferably from 40 to 65 theoretical plates. The reflux ratio is, depending on the number of theoretical plates realized and the required purity of the isobutene, preferably less than 60, more preferably less than 40. The operating pressure of the column K2 can preferably be set to from 0.1 to 2.0 MPa$_{(abs)}$. The pressure includes all values and subvalues therebetween, especially including 0.2, 0.3, 0.4, 0.5, 0.6, 0.7, 0.8, 0.9, 1, 1.1, 1.2, 1.3, 1.4, 1.5, 1.6, 1.7, 1.8, and 1.9 MPa$_{(abs)}$.

A work-up of isobutene by extraction and distillation is described in detail in, for example, DE 102 38 370. Methanol is preferably separated off from the isobutene-containing overhead stream (V) obtained in process step c) by extraction and dimethyl ether and, if desired, water are separated off by distillation from the extracted isobutene in process step f).

The isobutene obtained in this way can, for example, have the composition shown in Table 2:

TABLE 2

| Typical composition of commercial isobutene Proportions by mass [kg/kg] | |
|---|---|
| $C_3$-Hydrocarbons | <0.000100 |
| Butanes | <0.001000 |
| Isobutene | >0.999000 |
| 1-Butene/2-butenes | <0.001000 |
| Methanol | <0.000030 |
| $C_5$-Hydrocarbons | <0.000500 |
| Water | <0.000050 |

However, depending on purity requirements, lower concentrations of the secondary components are also conceivable if necessary.

The isobutene prepared by the process of the invention can, for example, be used for the preparation of methallyl chloride, methallylsulphonates, methacrylic acid or methyl methacrylate. In particular, it can be advantageous for both the methanol and the isobutene to be separated off from the dissociation product and for both the methanol and the isobutene to be used for the preparation of methyl methacrylate. Such a process for preparing methyl methacrylate is described, for example, in EP 1 254 887, which is expressly incorporated by reference.

Starting Material

MTBE of differing quality can be used as MTBE-containing stream (I) in process step a). In particular, it is possible to use industrial MTBE of various qualities or mixtures of industrial MTBE and methanol as stream (I). Industrial MTBE (fuel grade) is the preferred starting material. Table 3 shows, for example, the typical composition of an industrial MTBE from OXENO Olefinchemie GmbH.

TABLE 3

| Typical composition of industrial MTBE (fuel grade) from Oxeno Proportions by mass [kg/kg] | |
|---|---|
| 1-Butene/2-butenes | 0.001000 |
| Pentanes | 0.001500 |
| MTBE | 0.978000 |
| 2-Methoxybutane | 0.003000 |
| Methanol | 0.008500 |
| tert-Butanol | 0.003000 |
| Water | 0.000050 |
| Diisobutene | 0.003300 |

Industrial MTBE can be prepared by known methods by reacting $C_4$-hydrocarbon mixtures from which the multiply unsaturated hydrocarbons have largely been removed, for example raffinate I or selectively hydrogenated cracking $C_4$, with methanol. A process for preparing MTBE is described, for example, in DE 101 02 062.

In the process of the invention, a mixture of industrial MTBE and a substream of the dissociation product (IV) which has been separated off by distillation is used as stream (I). The substream here is the stream (VIII) obtained in process step d) by fractionation of the bottom product (VI).

It can be particularly advantageous in the process of the invention for an MTBE-containing stream which is entirely or partly obtained by removing low boilers from an MTBE-containing stream Ia in an optional process step g) to be used as stream (I).

The removal of low boilers can be particularly advantageous when the MTBE-containing stream Ia comprises, for example, $C_4$- or $C_5$-hydrocarbons. The separation of the low boilers from stream Ia in the optional process step g) can preferably be carried out in a distillation column. The distillation column is preferably operated so that the low boilers can be separated off as overhead product.

The process step g) is preferably carried out in a distillation column which has from 30 to 75 theoretical plates, preferably from 40 to 65 theoretical plates and particularly preferably from 40 to 55 theoretical plates. The column is, depending on the number of theoretical plates realized, the composition of the MTBE used and the required purity of $C_4$- and $C_5$-hydrocarbons, preferably operated at a reflux ratio of from 150 to 350, in particular from 200 to 300. The column in the optional process step g) is preferably operated at a pressure of from 0.2 to 0.6 $MPa_{(abs)}$, more preferably from 0.3 to 0.4 $MPa_{(abs)}$. The column can be heated using, for example, steam. The condensation can, depending on the operating pressure selected, be carried out by means of cooling brine, cooling water or air. The vapour from the top of the column can be completely or only partially condensed, so that the overhead product IX can be taken off in either liquid or vapour form. The overhead product IX can be utilized thermally or be used as starting material for a synthesis gas plant.

Figure 1:
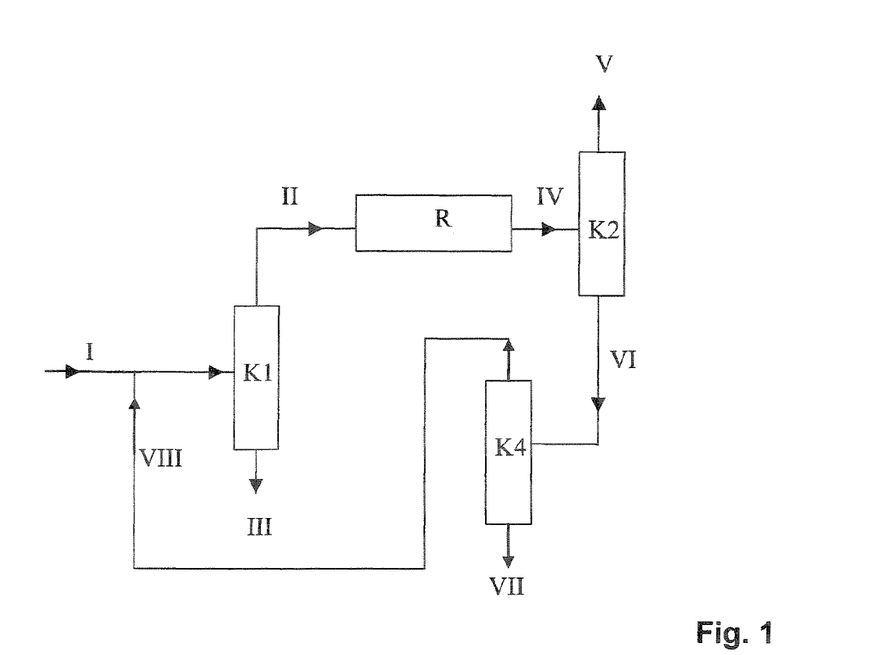
FIG. 1 shows a block diagram of an embodiment of a plant in which the process of the invention can be carried out.
Figure 2:
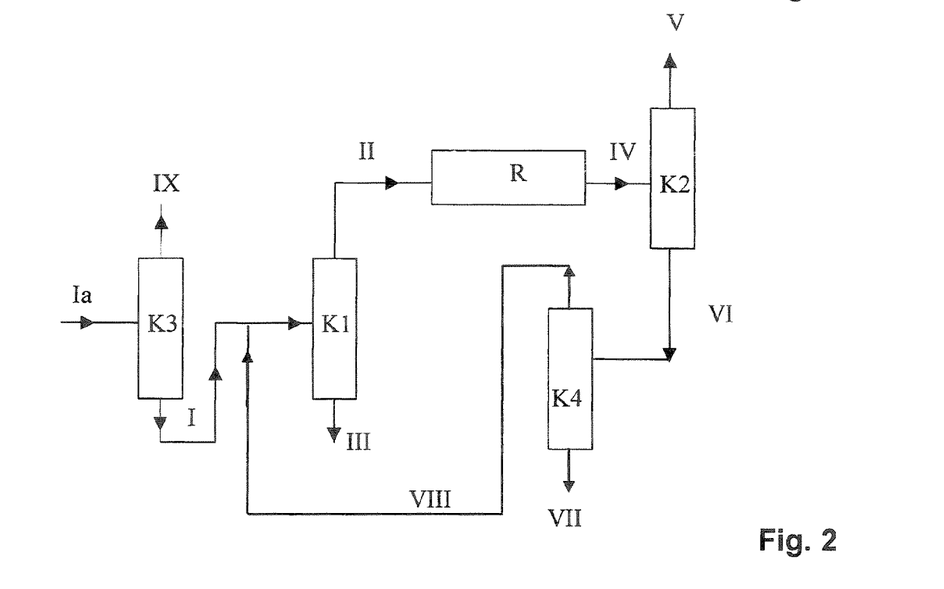
FIG. 2 shows a block diagram of another embodiment of a plant in which the process of the invention can be carried out.

If columns such as the columns denoted by K1, K2 and K3 in FIG. 1 or FIG. 2 are used in the process of the invention, these can be provided with internals such as trays, rotating internals, irregular beds and/or ordered packing.

In the case of column trays, the following types, for example, can be used:
trays having holes or slits in the tray plate;
trays having necks or chimneys which are covered by bubble caps, covers or hoods;
trays having holes in the tray plate which are covered by movable valves;
trays having special constructions.

In columns having rotating internals, the runback can, for example, be sprayed by means of rotating funnels or spread as a film on a heated tube wall by means of a rotor.

As mentioned above, columns having irregular beds of various packing elements can be used in the process of the invention. The packing elements can comprise virtually all materials, in particular steel, stainless steel, copper, carbon, stoneware, porcelain, glass or plastics, and have a wide variety of shapes, in particular spheres, rings having smooth or profiled surfaces, rings having internal struts or openings through the wall, wire meshes, saddle bodies and spirals.

Packings having a regular/ordered geometry can, for example, comprise metal sheets or meshes. Examples of such packings are Sulzer mesh packings BX made of metal or plastic, Sulzer lamella packings Mellapak made of sheet metal, high-performance packings from Sulzer such as Mella-pakPlus, structured packings from Sulzer (Optiflow), Montz (BSH) and Kühni (Rombopak).

The present invention is illustrated below with reference to FIGS. 1 and 2, without the invention being restricted to the embodiments depicted by way of example there.

A block diagram of an embodiment of a plant in which the process of the invention can be carried out is shown in FIG. 1. The MTBE-containing feed stream (I) is mixed with the recycle stream (VIII) and, in process step a), separated in the column K1 into a bottom product (III) which contains the secondary components having boiling points higher than that of MTBE, for example diisobutene and 2-methoxybutane, and an MTBE-containing overhead product (II). The MTBE present in the overhead product (II) is mostly dissociated into isobutene and methanol in process step b) in the reactor R. The dissociation product (IV) obtained in process step b) in reactor R is fractionated in process step c) in the column K2 to give an isobutene-containing mixture (V) containing methanol and possibly dimethyl ether and a bottom product (VI) containing unreacted MTBE, methanol and secondary components. The bottom product (VI) from process step c) is separated in process step d) in column K4 into a bottom product (VII) comprising, in particular, methanol and an MTBE-containing overhead product (VIII) which, in process step e), is recirculated to process step a). The column K2 can optionally be configured as a reactive distillation column.

A block diagram of a further embodiment of a plant in which the process of the invention can be carried out is shown in FIG. 2. The embodiment of FIG. 2 differs from that of FIG. 1 in that the feed MTBE Ia is separated in a preliminary column K3 into an overhead product (VII) comprising low boilers such as $C_4$- and $C_5$-hydrocarbons and an MTBE-containing stream (I) which has been freed of low boilers and is mixed with the recycle stream (VIII) and fed into the column K1.

Having generally described this invention, a further understanding can be obtained by reference to certain specific examples which are provided herein for purposes of illustration only, and are not intended to be limiting unless otherwise specified.

EXAMPLES

Example a

Production of a Shaped Aluminosilicate Body 500 g of aluminosilicate powder (manufacturer: Grace Davison, grade: Davicat O 701, formal $Al_2O_3$ content: 13% by mass, formal $SiO_2$ content: 76% by mass, formal $Na_2O$ content: 0.1% by mass, loss on ignition at 850° C.: about 11%), 363 g of Disperal gel (formal $Al_2O_3$ content: 15.6%), which was obtained by stirring 197 g of Disperal, a boehmite having a formal $Al_2O_3$ content of 77% by mass from Sasol Deutschland GmbH, into 803 g of a 1.28% strength by mass aqueous nitric acid, subsequently stirring vigorously so that the gel being formed was continually sheared and was thus kept in a fluid state in a covered container for 3 hours at 60° C., cooling the gel to room temperature and replacing any water which had evaporated, and 370 g of deionized water were firstly mixed thoroughly with one another in a high-intensity mixer from Eirich. Pelletization was subsequently carried out in the high-intensity mixer from Eirich, giving uniform roundish pellets having a diameter of from about 1 to 3 mm over a period of 30-40 minutes. The moist pellets were firstly dried at 120° C. in a stream of air and subsequently heated at 2 K/min to 550° C. and calcined at this temperature for 10 hours in a stream of air. The aluminosilicate pellets produced in this way formally contained 76% by mass of $Al_2O_3$ and 24% by mass of $SiO_2$. In addition, the catalyst produced contained 0.12% by mass of sodium compounds (calculated as sodium oxide). The composition of the aluminosilicate pellets was calculated from the amount and composition of the starting substances. The aluminosilicate pellets had a pore volume determined by the above-described cyclohexane method of 1.15 ml/g.

Example b

Production of a Shaped Catalyst (According to the Invention)

An impregnation solution having a magnesium content of 4.7% by mass was produced from deionized water and magnesium nitrate hexahydrate. The pH of this solution was 5.1. A sieve fraction of the aluminosilicate support produced in Example 1 (diameter: 1.0 mm-2.8 mm) was impregnated with the acidic magnesium nitrate solution by vacuum impregnation. For this purpose, the pellets were placed in a glass tube and the latter was evacuated for about 30 minutes (water pump vacuum of about 25 hPa). The impregnation solution was subsequently sucked in from the bottom to above the upper surface of the bed of solid. After a contact time of about 15 minutes, the solution which had not been taken up by the support was drained. The moist pellets were firstly dried to constant weight at 140° C. in a stream of air and subsequently heated at 3 K/min to 450° C. and calcined at this temperature for 12 hours. The catalyst produced formally comprised 68% by mass of silicon dioxide, 21% by mass of aluminium oxide and 11% by mass of magnesium oxide. In addition, the catalyst produced contained 0.11% by mass of sodium compounds (calculated as sodium oxide). The composition of the catalyst was calculated from the amount and composition of the starting substances and of the impregnation solution which had been drained off. The amounts of sodium were a constituent of the aluminosilicate used in Example 1. The pore volume determined by the above-described cyclohexane method was 1.1 ml/g.

The following example calculations were carried out using the steady-state simulation program ASPEN Plus (version 12.1 from AspenTech). To produce transparent, reproducible data, only generally available materials data were used. In addition, the use of a reactive distillation was dispensed with in all variants. These simplifications make it readily possible for a person skilled in the art to reproduce the calculations. Although the methods used do not have sufficient accuracy for the design of industrial plants, the qualitative differences between the arrangements were correctly determined, In all variants demonstrated, the MTBE conversion can be increased by use of a reactive distillation.

The Property Method "UNIFAC-DMD" (see J. Gmehling, J. Li, and M. Schiller, Ind. Eng. Chem. Res. 32, (1993), pp. 178-193) was used in the examples. Modelling was in each case based on a reactor volume of the reactor R of 100 l, assuming a charge of a catalyst which formally comprises magnesium oxide, aluminium oxide and silicon oxide and whose production was described in Examples a and b.

For modelling of the reactor, a kinetic reactor model based on comprehensive experimental measured data using this catalyst was used in the calculations. The reaction temperatures assumed in the modelling of the reactor were therefore also reported in the examples. Since the composition of the inflowing and outflowing streams of the reaction stage were also reported in each case, a person skilled in the art can, by reproducing the reactors with prescribed conversions, repeat the calculation of the example without knowing the precise equations for the kinetics. The reactor pressure was 0.8 MPa$_{(abs)}$ in all examples.

Example 1

Example 1 corresponds to the variant shown in FIG. 1. An MTBE stream (I) (feed MTBE) of 100 kg/h having the composition shown in Table 4 (typical fuel MTBE, cf. Table 1) was assumed as feed to the MTBE dissociation plant, as shown in FIG. 1. Since it was assumed in this example that a relatively high concentration of linear butenes, saturated $C_4$-hydrocarbons and $C_5$-hydrocarbons in the isobutene product was not a problem, a column K3 as shown in FIG. 2 can be omitted and column K1 can be utilized only for the removal of diisobutene.

TABLE 4

Composition of the assumed MTBE inflow stream into the MTBE dissociation plant for Example 1

| | Feed MTBE (I) |
|---|---|
| Mass flow [kg/h] | 100.00 |
| Proportions by mass [kg/kg] | |
| Dimethyl ether | |
| Isobutene | |
| 1-Butene/2-butenes | 0.001000 |
| $C_5$-Hydrocarbons | 0.001500 |
| MTBE | 0.979650 |
| 2-Methoxybutane | 0.003000 |
| Methanol | 0.008500 |
| tert-Butanol | 0.003000 |
| Water | 0.000050 |
| Diisobutene | 0.003300 |

The feed MTBE (I) was mixed with the recycle stream (VIII) to give the MTBE stream which was introduced as feed into the column K1. The recycle stream (VIII) was the distillate stream from column K4, which contains all of the MTBE which had not been reacted in the reaction section (R), the secondary components diisobutene and 2-methoxybutane and methanol. The assumed composition of the recycle stream (VIII) and of the feed stream to the column K1 obtained by this mixing is shown in Table 5.

TABLE 5

Composition of the recycle stream (VIII) and of the feed stream to the column K1 for Example 1

| | Recycle stream (VIII) | Feed to K1 |
|---|---|---|
| Mass flow [kg/h] | 15.64 | 115.64 |
| Proportions by mass [kg/kg] | | |
| Dimethyl ether | 0.000051 | 0.000007 |
| Isobutene | 0.003168 | 0.000428 |
| 1-Butene/2-butenes | 0.000161 | 0.000887 |
| $C_5$-Hydrocarbons | 0.010212 | 0.002678 |
| MTBE | 0.695113 | 0.941171 |
| 2-Methoxybutane | 0.063845 | 0.011228 |
| Methanol | 0.222966 | 0.037503 |
| tert-Butanol | 0.000007 | 0.002595 |
| Water | 0.000086 | 0.000055 |
| Diisobutene | 0.004391 | 0.003448 |

The separation task of the column K1 in Example 1 was the removal of diisobutene. The column had 52 theoretical plates and was operated at a reflux ratio of 1.2 and a pressure of 0.95 MPa$_{(abs)}$. The feed stream was introduced above plate 30 counted from the top. The temperature at the top was 140.7° C., and the temperature at the bottom was 181.2° C. A gaseous fraction which was free of diisobutene, cf. Table 6, was obtained as overhead product (II). The MTBE content was about 94.5% by mass. Since, as mentioned above, it was diisobutene in particular which was to be separated off, 2-methoxybutane was still present in an appreciable amount, viz. about 1.1% by mass. The MTBE content of the bottom product (III) was 24% by mass. The MTBE content of the bottom product can be reduced further by increasing the reflux ratio and/or the separation power.

TABLE 6

Composition of the distillate stream (II) and bottom stream (III) from column K1 for Example 1

|  | Distillate from K1 (II) | Bottom product from K1 (III) |
|---|---|---|
| Mass flow [kg/h] | 115.09 | 0.55 |
| Proportions by mass [kg/kg] |  |  |
| Dimethyl ether | 0.000007 |  |
| Isobutene | 0.000430 |  |
| 1-Butene/2-butenes | 0.000891 |  |
| $C_5$-Hydrocarbons | 0.002691 |  |
| MTBE | 0.944511 | 0.240000 |
| 2-Methoxybutane | 0.011125 | 0.032960 |
| Methanol | 0.037682 |  |
| tert-Butanol | 0.002607 | 0.000055 |
| Water | 0.000055 |  |
| Diisobutene |  | 0.726985 |

The distillate stream (II) from the column K1 is, after further heating to the reaction temperature, fed to the reaction section (R). The reactor was operated at 285° C. and 0.85 MPa$_{(abs)}$. Under these reaction conditions, an MTBE conversion of about 90% was obtained and the conversion of 2-methoxybutane was about 22%. The composition of the reactor output (IV) is shown in Table 7.

TABLE 7

Composition of the reactor output (IV) and of the distillate stream (V) and the bottom stream (VI) from column K2 for Example 1

|  | Reactor output (IV) | Distillate from K2 (V) | Bottom product from K2 (VI) |
|---|---|---|---|
| Mass flow [kg/h] | 115.09 | 65.55 | 49.54 |
| Proportions by mass [kg/kg] |  |  |  |
| Dimethyl ether | 0.002811 | 0.004923 | 0.000016 |
| Isobutene | 0.542440 | 0.951678 | 0.001000 |
| 1-Butene/2-butenes | 0.002449 | 0.004261 | 0.000051 |
| $C_5$-Hydrocarbons | 0.002691 | 0.002289 | 0.003223 |
| MTBE | 0.094451 | 0.000001 | 0.219413 |
| 2-Methoxybutane | 0.008677 |  | 0.020158 |
| Methanol | 0.343666 | 0.036580 | 0.749953 |
| tert-Butanol | 0.000574 |  | 0.001333 |
| Water | 0.001646 | 0.000269 | 0.003468 |
| Diisobutene | 0.000597 |  | 0.001386 |

The reactor output (IV) was partially condensed and fed as a two-phase mixture to the column K2. The column had 42 theoretical plates and was operated at a reflux ratio of 0.3 and a pressure of 0.65 MPa$_{(abs)}$. The feed stream was introduced above plate 28, counted from the top. The temperature at the top was 51.5° C., and the temperature at the bottom was 114.9° C. The overhead product (V) was isobutene having a purity of greater than 95% by mass of isobutene, cf. Table 7. As a result of 2-methoxybutane having been removed to only a slight extent in column K1, the content of linear butenes formed by dissociation of 2-methoxybutane was about 4300 ppm by mass and thus relatively high, but was still below 5000 ppm by mass. The isobutene product can thus be used for many industrial syntheses in which linear butenes in these concentrations do not interfere. If required, the methanol can be removed by extraction with water, and the residual water and the dimethyl ether can be removed by means of a subsequent distillation.

The bottom product (VI) from the column K2 comprises predominantly unreacted MTBE (about 22% by mass) and methanol (about 75% by mass). In addition, unreacted 2-methoxybutane, tert-butanol, water and diisobutene formed by reaction, inter alia, were present. This stream was fed to the column K4.

TABLE 8

Composition of the bottom stream (VII) from column K4 for Example 1

|  | Bottom product from K4 (VII) |
|---|---|
| Mass flow [kg/h] | 33.90 |
| Proportions by mass [kg/kg] |  |
| Dimethyl ether |  |
| Isobutene |  |
| 1-Butene/2-butenes |  |
| $C_5$-Hydrocarbons |  |
| MTBE |  |
| 2-Methoxybutane |  |
| Methanol | 0.993028 |
| tert-Butanol | 0.001944 |
| Water | 0.005028 |
| Diisobutene |  |

The column K4 had 35 theoretical plates and was operated at a reflux ratio of 2.8 and a pressure of 0.15 MPa$_{(abs)}$. The feed stream was introduced above plate 10, counted from the top. The temperature at the top was 60.8° C., and the temperature at the bottom was 75.0° C. The composition of the bottom product (VII) is shown in Table 8, and the composition of the distillate (VIII) from the column K4 is shown in Table 5. In the column, MTBE, 2-methoxybutane and diisobutene together with a small amount of methanol were distilled off at the top. The formation of an azeotrope of these components with methanol was utilized here. In addition, all low boilers (dimethyl ether, butenes and $C_5$-hydrocarbons) were also separated off, so that a very pure bottom product comprising over 99% by mass of methanol and containing water and tert-butanol as only secondary components can be obtained. The methanol therefore had a purity which was sufficiently high for it to represent a commercial product and be able to be used for customary industrial syntheses, for example esterifications or etherifications. If required, the methanol can also be concentrated to even higher purities in a further distillation step. The distillate (VIII) from the column K4 was mixed into the feed to the column K1.

Example 2

Example 2 corresponds to the variant shown in FIG. 2 with removal of $C_4/C_5$-hydrocarbons (low boilers) in the column K3. An MTBE stream (Ia) of 100 kg/h having a composition unchanged from Example 1, see Table 4, was assumed as feed to the MTBE dissociation plant. In contrast to Example 1, the column K1 in Example 2 was to separate off both diisobutene and 2-methoxybutane.

TABLE 9

Composition of the distillate stream (IX) and the bottom stream
from column K4 (I) for Example 2

|  | Distillate from K3 (IX) | Bottom product from K4 (I) |
|---|---|---|
| Mass flow [kg/h] | 0.30 | 99.70 |
| Proportions by mass [kg/kg] | | |
| Dimethyl ether | | |
| Isobutene | | |
| 1-Butene/2-butenes | 0.329909 | |
| $C_5$-Hydrocarbons | 0.470197 | 0.000075 |
| MTBE | 0.100004 | 0.982324 |
| 2-Methoxybutane | 0.000010 | 0.003009 |
| Methanol | 0.083474 | 0.008272 |
| tert-Butanol | | 0.003009 |
| Water | 0.016406 | |
| Diisobutene | | 0.003310 |

In the column K3, the $C_4$- and $C_5$-hydrocarbons were firstly separated from the MTBE stream (Ia) down to a residual content of 75 ppm by mass. The column had 52 theoretical plates and was operated at a reflux ratio of 205 and a pressure of 0.45 $MPa_{(abs)}$. The feed stream was introduced above plate 22, counted from the top. The temperature at the top was 59.0° C., and the temperature at the bottom was 107.3° C. The distillate from this column (IX) had a residual MTBE content of 10% by mass. The MTBE content can be reduced further by increasing the reflux ratio and/or number of theoretical plates. Table 9 shows the composition of the distillate stream (IX) and the bottom stream from the column K3.

The bottom product from column K3, which had largely been freed of low boilers, was mixed with the recycle stream (VIII) to form the MTBE stream. The recycle stream (VIII) was once again the distillate stream from column K4, which contains all of the MTBE which had not been reacted in the reaction section (R), the secondary components diisobutene and 2-methoxybutane and methanol. The assumed composition of the recycle stream (VIII) and of the feed stream to the column K1 formed by this mixing is shown in Table 10.

TABLE 10

Composition of the recycle stream (VIII) and the feed
stream to column K1 for Example 2

|  | Recycle stream (VIII) | Feed to K1 |
|---|---|---|
| Mass flow [kg/h] | 22.96 | 122.66 |
| Proportions by mass [kg/kg] | | |
| Dimethyl ether | 0.000044 | 0.000008 |
| Isobutene | 0.001230 | 0.000230 |
| 1-Butene/2-butenes | 0.000006 | 0.000001 |
| $C_5$-Hydrocarbons | 0.000176 | 0.000094 |
| MTBE | 0.742844 | 0.937497 |
| 2-Methoxybutane | 0.009274 | 0.004182 |
| Methanol | 0.243818 | 0.052363 |
| tert-Butanol | 0.000015 | 0.002449 |
| Water | 0.000176 | 0.000033 |
| Diisobutene | 0.002417 | 0.003143 |

The separation task of the column K1 in Example 2 was the removal of diisobutene and 2-methoxybutane. The column had 95 theoretical plates and was operated at a reflux ratio of 3.7 and a pressure of 0.95 $MPa_{(abs)}$. The feed stream was introduced above plate 32 counted from the top. The temperature at the top was 139.1° C., and the temperature at the bottom was 153.9° C. The overhead product obtained (II) was a gaseous fraction which was free of diisobutene and contains only 2100 ppm by mass of 2-methoxybutane, cf. Table 11. The MTBE content was about 94.5% by mass. The MTBE content of the bottom product (III) was about 63% by mass. The MTBE content of the bottom product can be reduced further by increasing the reflux ratio and/or the separation power.

TABLE 11

Composition of the distillate stream (II) and bottom stream (III)
from column K1 for Example 2

|  | Distillate from K1 (II) | Bottom product from K1 (III) |
|---|---|---|
| Mass flow [kg/h] | 120.91 | 1.75 |
| Proportions by mass [kg/kg] | | |
| Dimethyl ether | 0.000008 | |
| Isobutene | 0.000234 | |
| 1-Butene/2-butenes | 0.000001 | |
| $C_5$-Hydrocarbons | 0.000095 | |
| MTBE | 0.941924 | 0.631653 |
| 2-Methoxybutane | 0.002100 | 0.148053 |
| Methanol | 0.053121 | |
| tert-Butanol | 0.002483 | 0.000012 |
| Water | 0.000034 | |
| Diisobutene | | 0.220282 |

The distillate stream (II) from column K1 is, after further heating to the reaction temperature, fed to the reaction section (R). The reactor was operated at 270° C. and 0.85 $MPa_{(abs)}$. Under these conditions, an MTBE conversion of about 85% was obtained and the conversion of 2-methoxybutane was about 16%. The composition of the reactor output (IV) is shown in Table 12.

TABLE 12

Composition of the reactor output (IV) and of the distillate stream (V)
and the bottom stream (VI) of column K2 for Example 2

|  | Reactor output (IV) | Distillate from K2 (V) | Bottom product from K2 (VI) |
|---|---|---|---|
| Mass flow [kg/h] | 120.91 | 64.42 | 56.48 |
| Proportions by mass [kg/kg] | | | |
| Dimethyl ether | 0.002607 | 0.004877 | 0.000018 |
| Isobutene | 0.510937 | 0.958489 | 0.000500 |
| 1-Butene/2-butenes | 0.000216 | 0.000404 | 0.000002 |
| $C_5$-Hydrocarbons | 0.000095 | 0.000116 | 0.000071 |
| MTBE | 0.141063 | | 0.301946 |
| 2-Methoxybutane | 0.001761 | | 0.003770 |
| Methanol | 0.340740 | 0.035862 | 0.688455 |
| tert-Butanol | 0.000619 | | 0.001324 |
| Water | 0.001503 | 0.000251 | 0.002931 |
| Diisobutene | 0.000459 | | 0.000982 |

The reactor output (IV) was partially condensed and fed as a two-phase mixture to the column K2. Number of theoretical plates, point of introduction of the feed stream, reflux ratio and operating pressure of the column K2 were unchanged from Example 1. The temperature at the top was 51.4° C., and the temperature at the bottom was 114.5° C. The overhead product (V) was isobutene having a purity of greater than 95% by mass of isobutene. The limits for linear butenes required in a typical isobutene specification (<1000 ppm by mass) and those for $C_5$-hydrocarbons (<1000 ppm by mass) were reliably adhered to, cf. Tables 2 and 12. If required, the methanol can be removed by extraction of water, the residual water and the dimethyl ether can be separated off by means of a subsequent distillation and the isobutene can be concentrated to a purity of greater than 99.9% by mass. An isobutene which had been purified further in this way meets the specification given in Table 2.

The bottom product (VI) from the column K2 comprises predominantly unreacted MTBE (about 30% by mass) and methanol (about 69% by mass). In addition, unreacted 2-methoxybutane, tert-butanol, water and diisobutene formed by reaction, inter alia, were present. This stream was fed to the column K4.

TABLE 13

Composition of the bottom stream (VII) from column K4 for Example 2

| | Bottom product from K4 (VII) |
|---|---|
| Mass flow [kg/h] | 33.53 |
| Proportions by mass [kg/kg] | |
| Dimethyl ether | |
| Isobutene | |
| 1-Butene/2-butenes | |
| $C_5$-Hydrocarbons | |
| MTBE | |
| 2-Methoxybutane | |
| Methanol | 0.992963 |
| tert-Butanol | 0.002220 |
| Water | 0.004817 |
| Diisobutene | |

Number of theoretical plates, point of introduction of the feed stream and operating pressure of the column K4 were unchanged from Example 1. The reflux ratio was 1.7. The temperature at the top was 62.0° C., and the temperature at the bottom was 75.0° C. The composition of the bottom product (VII) is shown in Table 13, and the composition of the distillate (VIII) from the column K4 is shown in Table 10. In the column, MTBE, 2-methoxybutane and diisobutene together with a small amount of methanol were distilled off at the top. The formation of an azeotrope of these components with methanol was utilized here. In addition, all low boilers (dimethyl ether, butenes and $C_5$-hydrocarbons) were also separated off, so that a very pure bottom product comprising over 99% by mass of methanol and containing water and tert-butanol as only secondary components can be obtained. The methanol therefore had a purity which was sufficiently high for it to represent a commercial product and be able to be used for customary industrial syntheses, for example esterifications or etherifications. If required, the methanol can also be concentrated to even higher purities in a further distillation step. The distillate (VIII) from the column K4 was once again mixed into the feed to the column K1.

German patent application 10 2006 040 431.9 filed Aug. 29, 2006, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for preparing isobutene by dissociation of MTBE in the gas phase, comprising:
   a) fractional distillation of an MTBE-containing stream comprising feed MTBE (I) and a recycle stream (VIII) to give an MTBE-containing overhead stream (II) and a bottom stream (III) having a boiling point higher than MTBE,
   b) catalytic dissociation of the overhead stream (II) obtained in step a) to give a dissociation product (IV),
   c) separation by distillation of the dissociation product (IV) obtained in step b) into an overhead stream (V) comprising more than 90% by mass of isobutene and a bottom stream (VI) comprising diisobutene, MTBE and more than 50% of the methanol present in the dissociation product (IV),
   d) fractional distillation of the bottom stream obtained in step c) under conditions under which the methanol is obtained as bottom product (VII) and more than 99% of the MTBE is obtained in the overhead product (VIII), and
   e) recirculation of the overhead product (VIII) to step a).

2. The process according to claim 1, wherein the fractional distillation in step a) is carried out so that the stream (II) has a concentration of 2-methoxybutane of less than 2500 ppm by mass, based on MTBE.

3. The process according to claim 1, wherein the dissociation in step b) is carried out under conditions under which the conversion of MTBE is greater than the conversion of 2-methoxybutane.

4. The process according to claim 1, wherein the dissociation in step b) is carried out over a catalyst which has an activity with respect to the dissociation of MTBE which is at least 1% greater than the activity with respect to the dissociation of 2-methoxybutane.

5. The process according to claim 1, wherein the dissociation in step b) is carried out in a single pass at a conversion of MTBE of from 50 to 98%.

6. The process according to claim 1, wherein industrial MTBE is used as stream (I).

7. The process according to claim 1, wherein in a further process step f), methanol is separated off by extraction and dimethyl ether is separated off by distillation from the isobutene-containing overhead stream (V) obtained in process step c).

8. The process according to claim 1, wherein an MTBE-containing stream which is entirely or partly obtained by removing low boilers from an MTBE-containing stream (Ia) is used as stream (I).

9. The process according to claim 1, wherein step a) is carried out at a pressure of from 0.1 to 2.0 $MPa_{(abs)}$.

10. The process according to claim 1, wherein step b) is carried out at a temperature of from 200 to 400° C.

11. The process according to claim 1, wherein step c) is carried out at a pressure of from 0.1 to 2.0 $MPa_{(abs)}$.

12. The process according to claim 1, wherein step c) comprises a reactive distillation for dissociating MBTE to isobutene and methanol.

13. The process according to claim 1, wherein said reactive distillation is carried out at a temperature of from 60 to 140° C.

14. The process according to claim 1, wherein said reactive distillation is carried out at a pressure of from 0.1 to 1.2 $MPa_{(abs)}$.

15. The process according to claim 1, wherein step d) is carried out at a pressure of from 0.05 to 1.0 $MPa_{(abs)}$.

16. The process according to claim 7, wherein step f) is carried out at a temperature of from 15 to 50° C.

17. The process according to claim 1, wherein the fractional distillation (a) is carried out in a distillation column having a bottoms temperature higher than a top temperature.

18. The process according to claim 1, wherein the overhead stream (V) and the overhead product (VIII) each comprise methanol.

* * * * *